US012790582B2

(12) United States Patent
Lee et al.

(10) Patent No.: US 12,790,582 B2
(45) Date of Patent: Nov. 10, 2026

(54) *ESCHERICHIA COLI* HAVING 3-HYDROXYPROPIONATE PRODUCTION ABILITY, WITH 3-HYDROXYPROPIONATE PRODUCTION GENE INSERTED INTO SAME, AND USE THEREOF

(71) Applicant: LG CHEM, LTD., Seoul (KR)

(72) Inventors: Jungyeon Lee, Daejeon (KR); Min Kyung Sung, Daejeon (KR); Jae Hyung Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 182 days.

(21) Appl. No.: 18/696,177

(22) PCT Filed: Sep. 30, 2022

(86) PCT No.: PCT/KR2022/014761

§ 371 (c)(1),
(2) Date: Mar. 27, 2024

(87) PCT Pub. No.: WO2023/055174

PCT Pub. Date: Apr. 6, 2023

(65) Prior Publication Data

US 2024/0360405 A1 Oct. 31, 2024

(30) Foreign Application Priority Data

Sep. 30, 2021 (KR) ........................ 10-2021-0129844
Nov. 26, 2021 (KR) ........................ 10-2021-0166073

(51) Int. Cl.

| | |
|---|---|
| ***C12N 1/205*** | (2026.01) |
| ***C12N 9/02*** | (2006.01) |
| ***C12N 9/10*** | (2006.01) |
| ***C12N 9/22*** | (2006.01) |
| ***C12N 9/88*** | (2006.01) |
| ***C12P 7/52*** | (2006.01) |
| ***C12R 1/19*** | (2006.01) |

(52) U.S. Cl.

CPC ........... *C12N 1/205* (2021.05); *C12N 9/0008* (2013.01); *C12N 9/1085* (2013.01); *C12N 9/22* (2013.01); *C12N 9/88* (2013.01); *C12P 7/52* (2013.01); *C12N 2310/20* (2017.05); *C12R 2001/19* (2021.05); *C12Y 102/01003* (2013.01); *C12Y 205/01006* (2013.01); *C12Y 402/0103* (2013.01)

(58) Field of Classification Search

None
See application file for complete search history.

(56) References Cited

U.S. PATENT DOCUMENTS

| | | | |
|---|---|---|---|
| 9,476,070 | B2 | 10/2016 | Jung et al. |
| 2010/0281555 | A1 | 11/2010 | Kim et al. |
| 2015/0203878 | A1 | 7/2015 | Rivas et al. |
| 2016/0145646 | A1 | 5/2016 | Frendewey et al. |
| 2018/0312852 | A1 | 11/2018 | Park et al. |
| 2023/0348942 | A1 | 11/2023 | Jo et al. |

FOREIGN PATENT DOCUMENTS

| | | | |
|---|---|---|---|
| EP | 4242312 | A1 | 9/2023 |
| JP | 2005-237209 | A | 9/2005 |
| KR | 10-2004-0041165 | A | 5/2004 |
| KR | 10-2009-0022978 | A | 3/2009 |
| KR | 10-2009-0058077 | A | 6/2009 |
| KR | 10-2014-0094364 | A | 7/2014 |
| KR | 10-2015-0004830 | A | 1/2015 |
| KR | 10-2016-0146588 | A | 12/2016 |
| KR | 10-2017-0102234 | A | 9/2017 |
| KR | 10-2020-0051375 | A | 5/2020 |
| KR | 10-2020-0053258 | A | 5/2020 |
| KR | 10-2021-0028779 | A | 3/2021 |
| KR | 10-2021-0036632 | A | 4/2021 |

OTHER PUBLICATIONS

Kwak et al., Biosynthesis of 3-hydroxypropionic acid from glycerol in recombinant *Escherichia coli* expressing Lactobacillus brevis dhaB and dhaR gene clusters and *E. coli* K-12 aldH, Bioresource Technology, 2013, vol. 135, pp. 432-439.

Kim et al., High-level production of 3-hydroxypropionic acid from glycerol as a sole carbon source using metabolically engineered *Escherichia coli*, Biotechnology and Bioengineering, 2020, vol. 117, No. 7, pp. 2139-2152.

Kim et al., Enhanced production of 3-hydroxypropionic acid from glycerol by modulation of glycerol metabolism in recombinant *Escherichia coli*, Bioresource Technology, 2014, vol. 156, pp. 170-175.

International Search Report issued for International Application No. PCT/KR2022/014761 on Jan. 9, 2023, 7 pages.

Tarasava et al. "Combinatorial pathway engineering using type I-E CRISPR interference" Biotechnology and Bioengineering, 2018, 115: 1878-1883.

*Primary Examiner* — Oluwatosin A Ogunbiyi
(74) *Attorney, Agent, or Firm* — ROTHWELL, FIGG, ERNST & MANBECK, P.C.

(57) ABSTRACT

The present specification pertains to a microorganism and/or *Escherichia coli* and a use thereof, wherein the microorganism and/or *Escherichia coli* has 3-hydroxypropionic acid or 3-hydroxypropionate (3-HP) production ability, with a foreign 3-HP production gene inserted into the genomic DNA thereof, and has a use of measuring the production ability of the inserted 3-HP production gene.

15 Claims, 5 Drawing Sheets

Specification includes a Sequence Listing.

【FIG. 1】
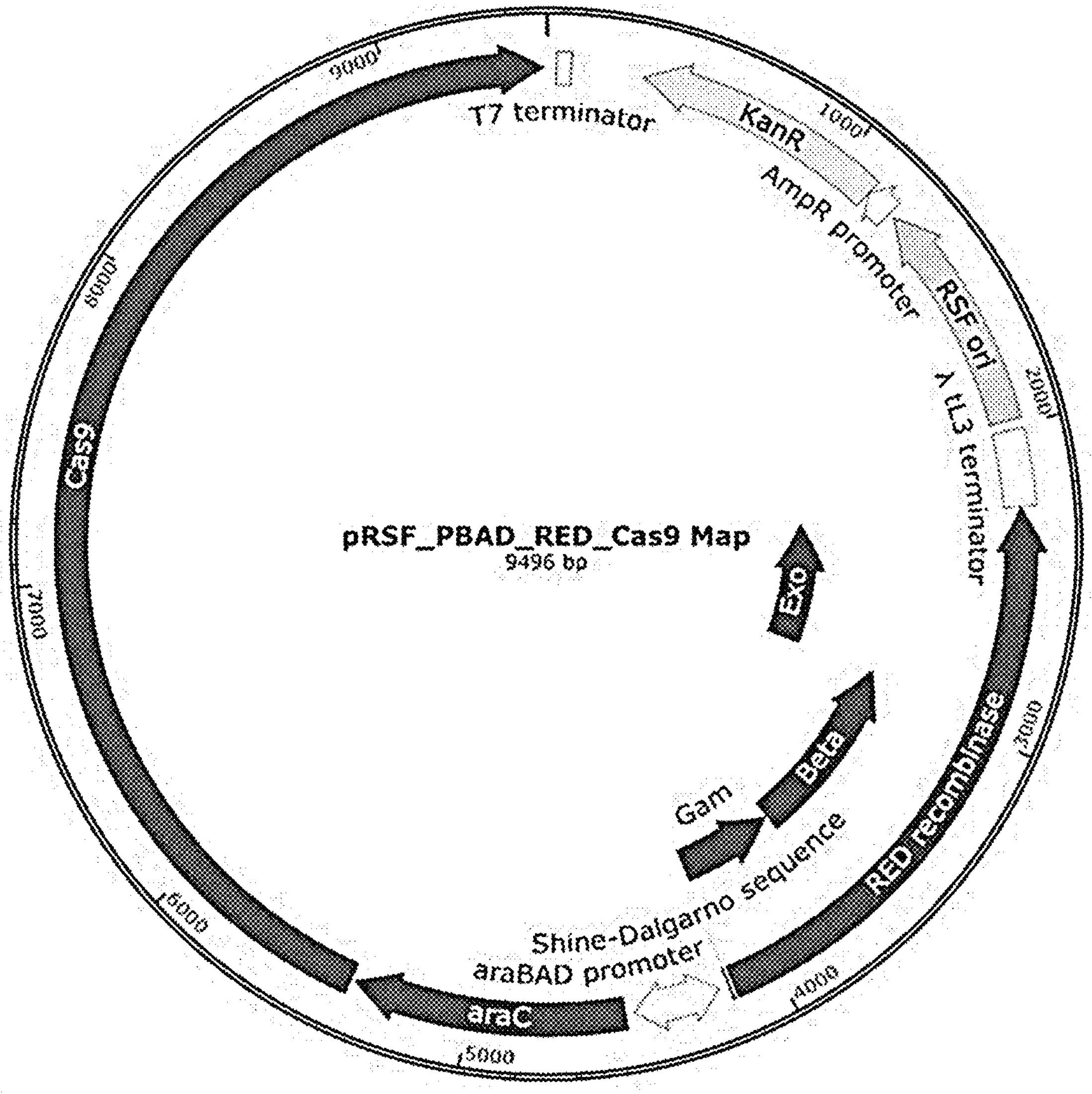

【FIG. 2】
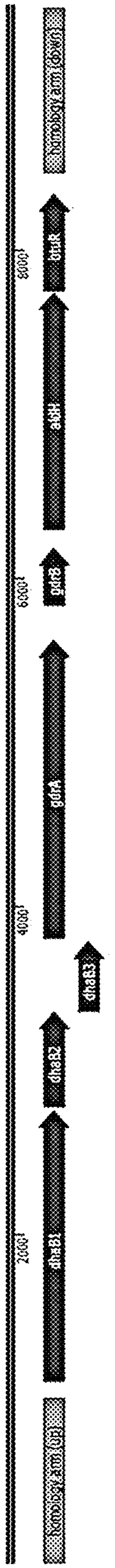

【FIG. 3】
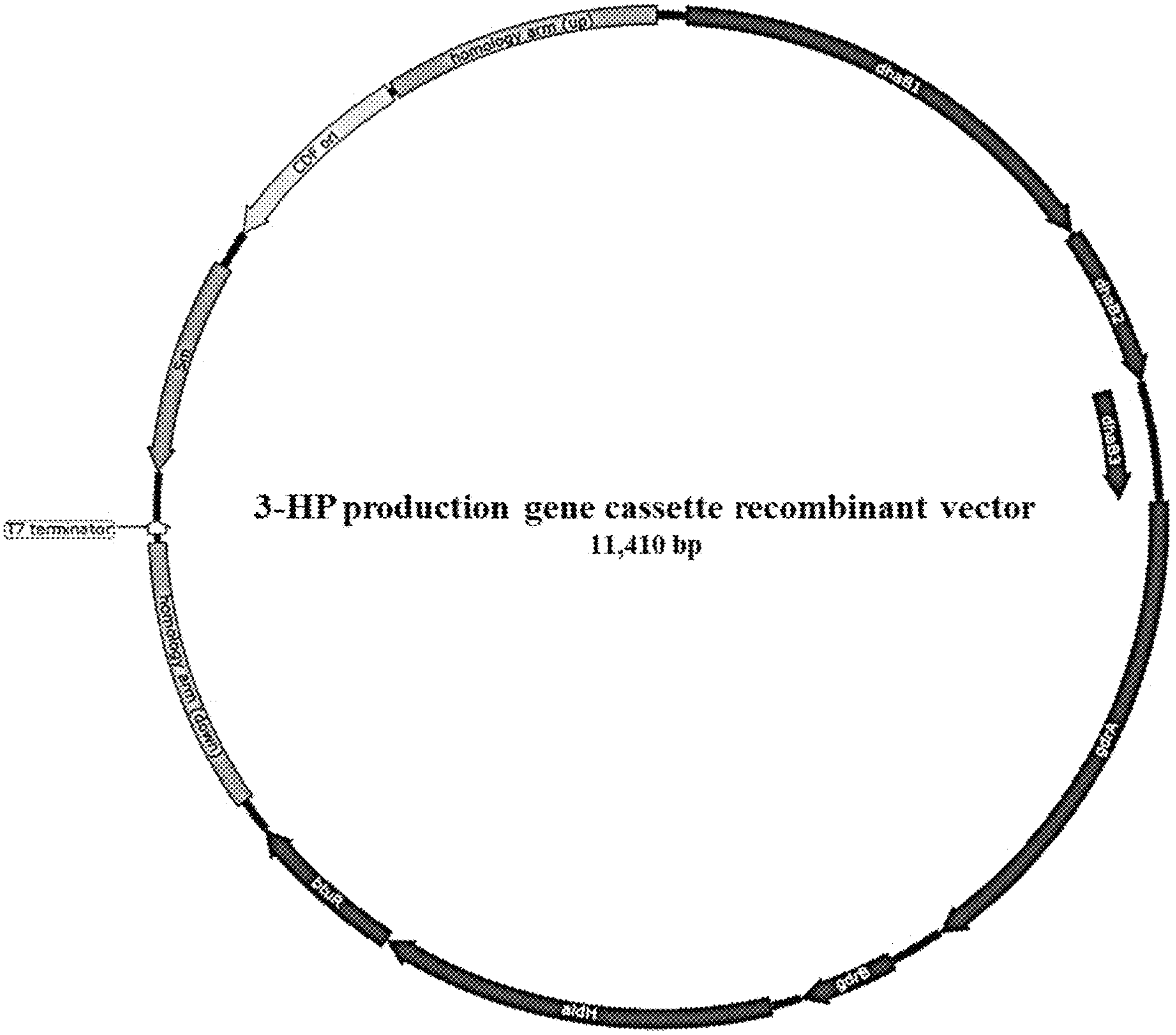

【FIG. 4】
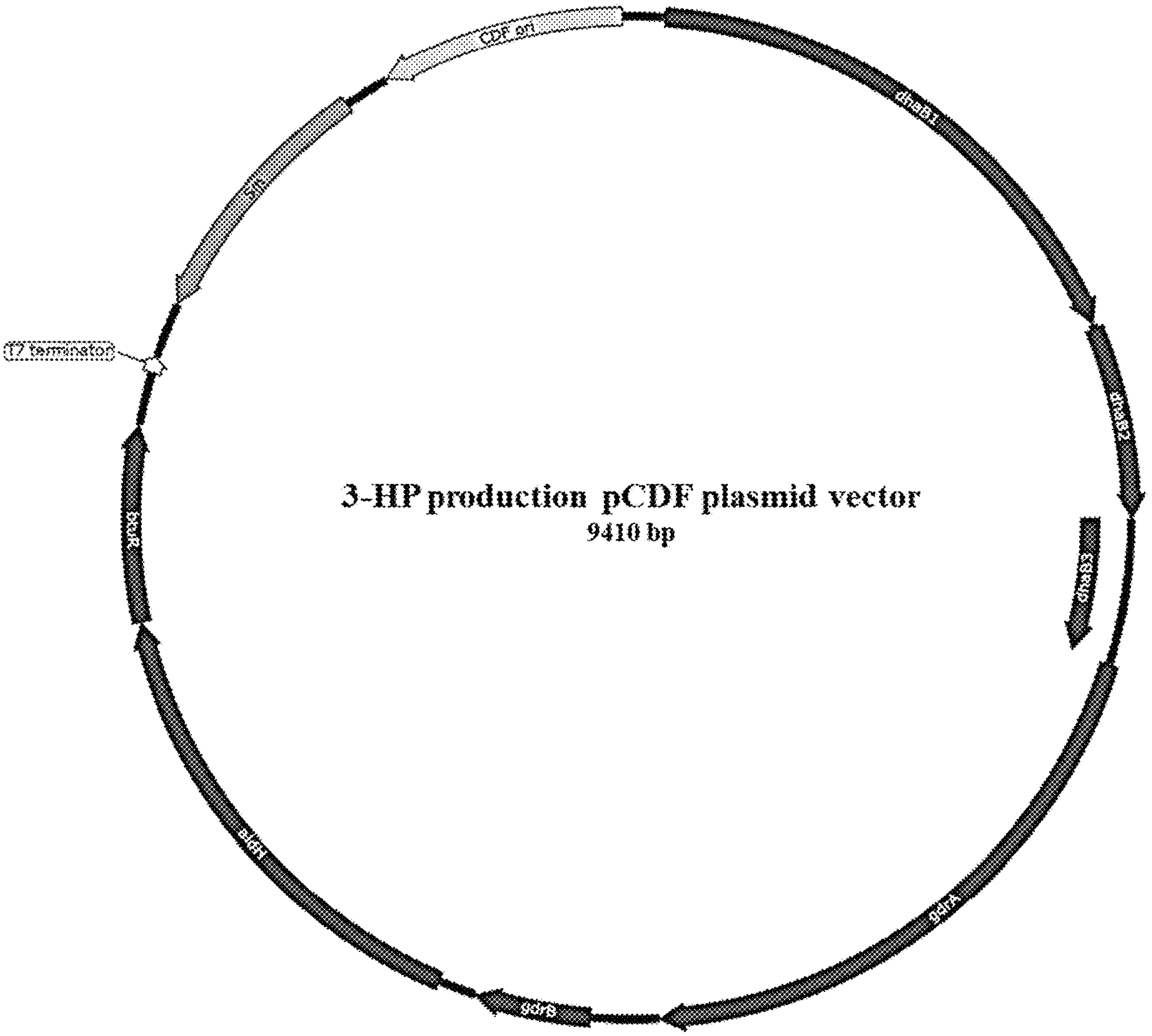

【FIG. 5】
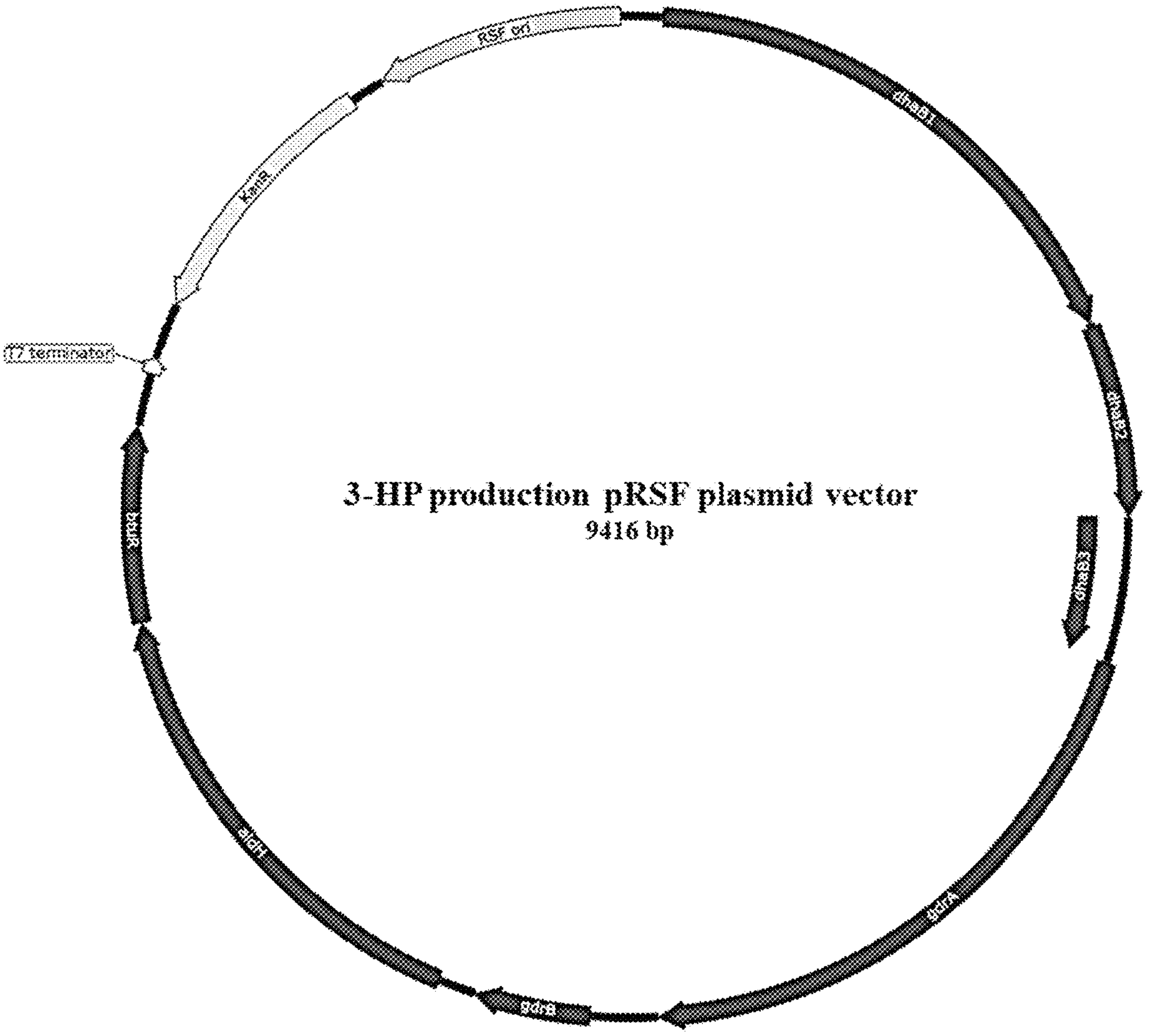

*ESCHERICHIA COLI* HAVING 3-HYDROXYPROPIONATE PRODUCTION ABILITY, WITH 3-HYDROXYPROPIONATE PRODUCTION GENE INSERTED INTO SAME, AND USE THEREOF

CROSS-REFERENCE TO RELATED APPLICATION(S)

The present application is a 35 U.S.C. § 371 National Phase Entry Application from PCT/KR2022/014761, filed on Sep. 30, 2022, which claims the benefit of priority based on Korean Patent Application No. 10-2021-0129844 filed on Sep. 30, 2021 and Korean Patent Application No. 10-2021-0166073 filed on Nov. 26, 2021, and the entire contents disclosed in the documents of the corresponding Korean patent applications are incorporated as a part of the present description.

TECHNICAL FIELD

The present application includes a Sequence Listing filed in electronic format. The Sequence Listing is entitled "OPP20223949KR_SEQ.xml" created on Sep. 30, 2022 and is 174,256 bytes in size. The information in the electronic format of the Sequence Listing is part of the present application and is incorporated herein by reference in its entirety.

It relates to a microorganism and/or *Escherichia coli* having 3-hydroxypropionic acid (3-hydroxypropionate, 3-HP) producing ability, in which a foreign 3-hydroxypropionic acid (3-hydroxypropionate, 3-HP) producing gene is inserted into the genomic DNA, and uses thereof, and a method for determining 3-HP producing ability of the 3-HP producing gene inserted into genomic DNA of the *Escherichia coli* (*E. coli*) bacterium, comprising culturing the microorganism and/or *E. coli* bacterium.

BACKGROUND

3-Hydroxypropionic acid (3-hydroxypropionic acid, 3-HP) is an important synthetic intermediate used in various chemical processes, and is a platform compound which can be converted into a variety of chemicals including acrylic acid, methyl acrylate, acrylamide, 1,3-propanediol, ethyl 3-HP, malonic acid, propiolactone and acrylonitrile, and the like. In addition, it has been actively studied in academia and industry, since it was selected as Top 12 value-added biochemical by U.S. Department of Energy (DOE).

3-HP can be produced through a chemical process using ethylene cyanohydrin, beta-iodopropionic acid, beta-bromopropionic acid, beta-chloropropionic acid, beta-propiolactone, acrylic acid, and the like as an intermediate, and can be produced through a biological process from glycerol. However, most of these chemicals have problems that they are toxic and carcinogenic, and consume a large amount of energy under the condition of high temperature and pressure, and discharge pollutants in large quantities.

Production of 3-HP is largely made up of two methods which are a chemical method and a biological method, but in case of the chemical method, as the initial material is expensive and toxic substances are generated during the production process, it is pointed out that it is not eco-friendly, so an eco-friendly bio-process is in the spotlight.

For 3-HP biosynthesis using a microorganism, conventionally, studies of one-step fermentation methods in which 3-HP production and cell growth occur simultaneously have been mainly studied, but there was a problem that the yield and productivity of 3-HP decreased as the substrate for 3-HP production was also used for cell growth and by-products such as acetate or lactate are generated, so it was tried to be improved through a 2-step preparation method in which 3-HP production and cell growth are performed separately.

However, in case of *E. coli* bacterium having a plasmid vector comprising a gene set for producing 3-HP from glycerol, it could not produce 3-HP when the 2-step culturing was applied in which cell growth and 3-HP production are separated using a culture medium and a minimal medium in a flask, and due to this, the 2-step culturing could not be applied, so it was necessary to simultaneously add a carbon source for cell growth and a carbon source consumed for 3-HP conversion into the minimal medium and the growth and proceed growth and production at the same time, and therefore, the cell concentration was low, and thus, it was not suitable for evaluating performance of a recombinant gene.

In addition, when culturing *E. coli* bacterium having the plasmid vector comprising the gene set, antibiotic input was essential to keep the vector maintenance and productivity constant, and concerns about antibiotic input cost and environmental contamination were raised accordingly, and the 3-HP production of the *E. coli* bacterium having the plasmid vector did not increase in proportion to the copy number, so it was difficult to measure the 3-HP producing ability of the gene in the plasmid vector.

DISCLOSURE

Technical Problem

Under the above circumstance, the present inventors have confirmed 3-HP production through a 2-step preparation method in which 3-HP production and cell growth are performed separately by inserting a foreign 3-hydroxypropionic acid (3-hydroxypropionate, 3-HP) producing gene into genomic DNA, and have confirmed that the 3-HP production is proportional to the copy number of the genomic DNA inserted gene, thereby completing the present invention.

One embodiment provides a microorganism (for example, *E. coli* bacterium) having 3-HP producing ability, in which a foreign 3-HP producing gene is inserted into genomic DNA with at least one copy number.

Another embodiment provides a composition for determining 3-HP producing ability of the 3-HP producing gene inserted into genomic DNA of the microorganism (for example, *E. coli* bacterium).

Other embodiment provides a method for determining 3-HP producing ability of the 3-HP producing gene inserted into genomic DNA of the microorganism (for example, *E. coli* bacterium), comprising culturing a microorganism (for example, *E. coli* bacterium) having 3-HP producing ability, in which a foreign 3-hydroxypropionic acid (3-hydroxypropionate, 3-HP) producing gene is inserted into genomic DNA with at least one copy number.

Technical Solution

The present description provides technologies related to a microorganism and/or *E. coli* bacterium having 3-HP producing ability, in which a foreign 3-hydroxypropionic acid (3-hydroxypropionate, 3-HP) producing gene is inserted into the genomic DNA, and uses thereof, and a method for determining 3-HP producing ability of the 3-HP producing gene inserted in genomic DNA of the *E. coli* bacterium comprising culturing the microorganism and/or *E. coli* bacterium.

In the present description, "3-hydroxypropionic acid (3-hydroxypropionate, 3-HP)" corresponds to carboxylic acid, particularly, β-carboxylic acid, and is an acidic viscous liquid, and may be produced by a microorganism (for example, *E. coli* bacterium).

In the present description, "microorganism" may comprise a single cell bacterium, and for example, it may be the genus of *Escherichia* including *E. coli* bacterium.

In the present description, "*E. coli* bacterium" is the genus of *Escherichia*, and it may be *E. coli* DH5a, *E. coli* JM101, *E. coli* K12, *E. coli* W3110, *E. coli* X1776, *E. coli* B, and/or *E. coli* XL1-Blue.

One embodiment provides a microorganism (for example, *E. coli* bacterium) having 3-HP producing ability, in which a foreign 3-hydroxypropionic acid (3-hydroxypropionate, 3-HP) producing gene is inserted into genomic DNA with one copy number or more.

Another embodiment provides a method for determining 3-HP producing ability of a 3-HP producing gene in which genomic DNA of the microorganism (for example, *E. coli* bacterium), comprising culturing a microorganism (for example, *E. coli* bacterium) having 3-HP producing ability, in which a foreign 3-hydroxypropionic acid (3-hydroxypropionate, 3-HP) producing gene is inserted into genomic DNA with one copy number or more.

Other embodiment provides a composition for 3-HP production, comprising a microorganism (for example, *E. coli* bacterium) having 3-HP producing ability, in which a foreign 3-hydroxypropionic acid (3-hydroxypropionate, 3-HP) producing gene is inserted into genomic DNA with one copy number or more.

Other embodiment provides a method for producing 3-HP, comprising culturing a microorganism (for example, *E. coli* bacterium) having 3-HP producing ability, in which a foreign 3-hydroxypropionic acid (3-hydroxypropionate, 3-HP) producing gene is inserted into genomic DNA with one copy number or more. The method for producing 3-HP may further comprise separating and/or purifying 3-HP form the culture, after the culturing.

Other embodiment provides a use for determining 3-HP producing ability of a 3-HP producing gene inserted into the microorganism (for example, *E. coli* bacterium) genomic DNA of the microorganism (for example, *E. coli* bacterium) having 3-HP producing ability, in which a foreign 3-hydroxypropionic acid (3-hydroxypropionate, 3-HP) producing gene is inserted into genomic DNA with one copy number or more.

Other embodiment provides a use for 3-HP production of a microorganism (for example, *E. coli* bacterium) having 3-HP producing ability, in which a foreign 3-hydroxypropionic acid (3-hydroxypropionate, 3-HP) producing gene is inserted into genomic DNA with one copy number or more.

The 3-HP producing gene may comprise a gene of at least one enzyme selected from the group consisting of glycerol dehydratase, aldehyde dehydrogenase, glycerol dehydratase reactivase and adenosyltransferase, but not limited thereto.

The microorganism (for example, *E. coli* bacterium) may be one in which a gene selected from the group consisting of yghD, glpK, ldhA, ack-pta and gldA among endogenous genes is deleted, but not limited thereto.

In the culturing the microorganism (for example, *E. coli* bacterium), a gene selected from the group consisting of yghD, glpK, ldhA, ack-pta and gldA among genes of the *E. coli* bacterium may be deleted, but not limited thereto.

The 3-HP producing gene may be inserted where at least one gene selected from the group consisting of ldhA, gldA, glpK, yghD, mgsA, poxB, nfrA, fhuA, fadL, adhE, pflB and aldA genes in genome of the microorganism (for example, *E. coli* bacterium) is located, but not limited thereto.

The 3-HP producing gene may be inserted into genomic DNA by CRISPR-Cas9 system, but not limited thereto.

The microorganism (for example, *E. coli* bacterium) having 3-HP producing ability may have 3-HP producing ability increased in proportion to the copy number of the 3-HP producing gene, but not limited thereto.

Other embodiment provides a composition for determining 3-HP producing ability of the 3-HP producing gene inserted into genomic DNA of the microorganism (for example, *E. coli* bacterium), comprising the microorganism (For example, *E. coli* bacterium).

The determining 3-HP producing ability may be determining whether the 3-HP production produced by the *E. coli* bacterium is proportional to the copy number of the 3-HP producing gene inserted into genomic DNA of the *E. coli* bacterium, but not limited thereto.

The method for determining 3-HP producing ability of the 3-HP producing gene inserted into genomic DNA of the microorganism (for example, *E. coli* bacterium) may further comprise measuring the amount of 3-HP produced by the microorganism (For example, *E. coli* bacterium), but not limited thereto.

In the measuring the amount of 3-HP produced, by determining whether the 3-HP production produced by the *E. coli* bacterium is proportional to the copy number of the 3-HP producing gene inserted into genomic DNA of the *E. coli* bacterium, the 3-HP producing ability may be confirmed, but not limited thereto.

The method for determining 3-HP producing ability of the 3-HP producing gene inserted into genomic DNA of the microorganism (for example, *E. coli* bacterium) may not comprise administering an antibiotic, but not limited thereto.

The method for determining 3-HP producing ability of the 3-HP producing gene inserted into genomic DNA of the microorganism (for example, *E. coli* bacterium) may be characterized in that the 3-HP producing ability is increased in proportion to the copy number of the 3-HP producing gene, but not limited thereto.

In the method provided in the present description, the culturing the microorganism (for example, *E. coli* bacterium), may comprise, the first culturing step which is culturing in a medium comprising glucose and/or sucrose as a carbon source; and the second culturing step which is culturing in a medium comprising glycerol as a carbon source, but not limited thereto.

The medium of the second culturing step may not comprise glucose and/or sucrose as a carbon source, but not limited thereto.

Hereinafter, the present application will be described in more detail.

DETAILED DESCRIPTION

The microorganism according to one embodiment may have ability to synthesize an organic acid, and for example, it may have ability to synthesize 3-hydroxypropionic acid (or 3-HP producing ability). The microorganism according to one embodiment may be a strain genetically engineered so as to produce an organic acid, or to have ability to produce an organic acid or to intensify ability to produce an organic acid, by comprising a gene involved in organic acid production by itself. The organic acid production includes that produced in a strain, that is produced in a cell and secreted to outside of the cell, or a combination thereof.

In the present application, "having 3-HP producing ability" may mean a cell and/or a microorganism naturally having 3-HP producing ability, or a microorganism in which 3-HP producing ability is given to a parent strain having no 3-HP producing ability. It may be used to mean a case in which the microorganism has 3-HP producing ability by introducing a mutation according to one embodiment and/or a case in which the microorganism has 3-HP producing ability by introducing a mutation according to one embodiment into a microorganism having no 3-HP producing ability. For example, the microorganism of the genus *Escherichia* having 3-HP producing ability may mean a natural microorganism itself or a microorganism of the genus *Escherichia* having improved 3-HP producing ability by inserting an external gene related to 3-HP production mechanism or intensifying or inactivating an intrinsic gene.

In the present description, in the microorganism in which a foreign 3-hydroxypropionic acid (3-hydroxypropionate, 3-HP) producing gene is inserted into genomic DNA, insertion of the 3-HP producing gene into genomic DNA may be achieved by a composition and/or a system for multiple insertion of a target gene (for example, a foreign 3-hydroxypropionic acid (3-hydroxypropionate, 3-HP) producing gene) comprising the following, but not limited thereto:

(1) a recombinant vector, comprising a gene encoding Cas9 protein and a gene encoding recombinase ("common recombinant vector");

(2) a recombinant vector ("variable recombinant vector") set specific to a target site which is a site which is present on genome of a target cell and a target gene (for example, foreign 3-hydroxypropionic acid (3-hydroxypropionate, 3-HP) producing gene) is introduced into:

i) a recombinant vector comprising a temperature sensitive origin (ts origin) and a gene expressing guide RNA (gRNA) specific to the target site ("G recombinant vector"); and ii) a recombinant vector comprising a target gene and a homologous region before and after the target site at both ends of the gene, in which the PAM sequence (NNGG) in the homologous region is substituted with CAAA ("D recombinant DNA").

The composition for multiple insertion may not comprise an antibiotic-resistant gene in the common recombinant vector, G recombinant vector and D recombinant DNA. By not comprising an antibiotic-resistant gene, there are advantages in that the size of each vector may be kept small, and the metabolic burden of a target cell may be reduced, and a target gene may be repeatedly inserted without limitation of the number of genes which can be introduced by the antibiotic-resistant gene without the antibiotic-resistant gene.

In the present description, "copy number" may mean the total number of the 3-HP producing gene or 3-HP producing gene cassette repeated equally in the microorganism (host cell; for example, *E. coli* bacterium), and the 3-HP producing gene or 3-HP producing gene cassette may be artificially introduced (inserted) from the outside. The 3-HP producing gene or 3-HP producing gene cassette may be inserted into genome of the microorganism as suggested in the present application, and/or present outside the genome through a structure such as a plasmid and the like. The 3-HP producing gene may mean a coding gene of at least one enzyme involved in a metabolic pathway accompanied for 3-HP production, and for example, it may be at least one selected from the group consisting of dhaB1,2,3, gdrA, gdrB, araE (aldH), btuR and the like or a combination thereof, but not limited thereto.

The 3-HP producing gene cassette comprises a series of gene combination related to 3-HP production, and may necessarily comprise the 3-HP producing gene described above and further comprise an expression (transcription) regulatory factor and/or a linker and the like. In one specific embodiment, the 3-HP producing gene cassette may comprise a 3-HP producing gene (for example, at least one selected from the group consisting of dhaB1,2,3, gdrA, gdrB, araE (aldH), btuR and the like or a combination thereof), an expression regulatory factor and a linker, and may be in a size of about 7 kb, but not limited thereto, and for example, "the 3-HP producing gene was inserted into genomic DNA with 5 copy numbers or more" may mean that the above-mentioned 3-HP producing gene or 3-HP producing gene cassette of a total of 5 or more is inserted (repeated) into genome of a microorganism (host cell).

In the present description, "target cell" means a cell to be transformed, and the type may be selected without limitation within the range of the purpose of transformation. In one embodiment, the target cell may be a prokaryotic cell, and in another embodiment, the target cell may be a bacterial cell. In one embodiment, the target cell may include both gram negative groups and gram-positive groups, and in one specific embodiment, the target cell may be *E. coli* bacterium, but not limited thereto.

In the present description, "target gene" means a nucleic acid molecule to be inserted into genome of a target cell, and for example, it may be a foreign 3-hydroxypropionic acid (3-hydroxypropionate, 3-HP) producing gene.

In the present description, unless otherwise mentioned, the temperature means a Celsius temperature.

In the present description, unless otherwise mentioned, the base sequence was described from the 5' end to the 3' end, and the amino acid sequence was described from the N-terminus to the C-terminus.

In the present description, the composition and/or system for multiple insertion of a target gene comprises a common recombinant vector, comprising (1) a gene encoding Cas9 protein and a gene encoding recombinase.

The common recombinant vector does not require additional insertion after being first inserted into the target cell, so it can reduce burden on cells.

The common recombinant vector may comprise an operably linked inducible promoter, a gene encoding Cas9 protein and a gene encoding recombinase.

The inducible promoter may be used as being selected without limitation within the range of the purpose to regulate expression of the gene encoding Cas9 and/or gene encoding recombinase. In one example, the inducible promoter may be a promoter which is induced by arabinose.

The Cas9 protein performs a role of breaking (for example, double strand break (DSB)) by recognizing PAM (Protospacer adjacent Motif) among genome of the target cell. The PAM sequence may be NNGG sequence, and the "N" may be a "A", "T", "C" or "G" base.

The Cas9 protein may be derived from *Streptococcus* pyonenes, and may be encoded by the nucleic acid sequence of SEQ ID NO: 1, but not limited thereto.

When the double strand break produced by the Cas9 protein is not recovered by recombinase enzyme, and the like, cells die and are eliminated from the selection process, so it is possible to select cells without an antibiotic-resistant gene.

The recombinase may be selected without limitation within the range of the purpose for inserting a target gene into genome of a target cell based on a homologous region to be described later, and for example, it may be RED recombinase. In one embodiment, the recombinase enzyme may be encoded by the nucleic acid sequence of SEQ ID NO: 2, and when the target gene is inserted into genome in the target cell by the recombinase enzyme and therefore DSB is recovered, the death of the cell does not occur.

In the present description, the composition and/or system for multiple insertion of a target gene comprises (2) a variable recombinant vector set. The variable recombinant vector set comprises (i) a G recombinant vector (gRNA-containing) comprising a temperature sensitive origin and a gene expressing guide RNA (gRNA) specific to a target site, and (ii) a D recombinant DNA (Donor) comprising a target gene and a homologous region.

In the variable recombinant vector set, the gRNA and homologous region may be designed specifically to the target site according to the location of the target site of the target cell, and the design may be performed using a method known in the art without limitation.

The variable recombinant vector set comprises (i) a G recombinant vector comprising a temperature sensitive origin and a gene expressing guide RNA specific to a target site.

By culturing a transduced transformant at a certain temperature or more using the temperature sensitive origin, the G recombinant vector in the transformant may be removed.

In one embodiment, the certain temperature may be appropriately selected according to the type of the temperature sensitive origin, and for example, it may be 36 degrees Celsius or more, 37 degrees Celsius or more, 39 degrees Celsius or more, or 41 degrees Celsius or more, but not limited thereto.

It is possible to simply remove the G recombinant vector only by changing the G temperature, and it is possible to introduce a target gene by introducing a new G recombinant vector and a D recombinant vector specific to a new position, and thus multiple gene introduction is possible with a simple process.

The gene expressing guide RNA (gRNA) may be designed by appropriately selecting according to a target position at which a target gene is introduced by a person skilled in the art.

In one embodiment, the target gene of guide RNA may be at least one selected from the group consisting of ldhA, yghD, glpK, gldA, mgsA, poxB, nfrA, fhuA, fadL, adhE, pflB and aldA genes among genes of a host cell (*E. coli* bacterium), but not limited thereto.

In one embodiment, the guide RNA may be at least one selected from the group consisting of the nucleic acid sequences of SEQ ID NOs: 3 to 17, but not limited thereto.

In addition, in the target cell to be transformed, a gene to be targeted by the guide RNA may be deleted, but not limited thereto.

When the gene to be targeted by the guide RNA is deleted in the target cell, the body part of the gene may be deleted, and the head and tail parts of the corresponding gene may be remained, and the guide RNA may act by targeting the genes of the head and tail parts.

The variable recombinant vector set comprises D (Donor) recombinant DNA, comprising (ii) a target gene and a homologous region.

The D recombinant DNA may be introduced in a linear DNA form into the target cell, and in one embodiment, the linear DNA may be prepared by cleaving a vector using restriction enzyme, or amplifying by polymerase chain reaction (PCR). In addition, the D recombinant DNA may be a recombinant vector or a DNA strand.

The homologous region corresponds to upstream and downstream pf a target site, and is attached to the 5' end and 3' end of the target gene, respectively. The homologous region may be appropriately adjusted in its length as needed, and for example, it may be 50 to 1200 bp, 50 to 1000 bp, 50 to 800 bp, 50 to 700 bp, 50 to 600 bp, 50 to 500 bp, 100 to 1200 bp, 100 to 1000 bp, 100 to 800 bp, 100 to 700 bp, 100 to 600 bp, 100 to 500 bp, 200 to 1200 bp, 200 to 1000 bp, 200 to 800 bp, 200 to 700 bp, 200 to 600 bp, 200 to 500 bp, 300 to 1200 bp, 300 to 1000 bp, 300 to 800 bp, 300 to 600 bp, or 300 to 500 bp, respectively, but not limited thereto.

When the length of the homologous region is too short, the efficiency of homologous recombination may decrease, and when the homologous region is too long, the size of the vector to be introduced into a cell becomes too large, and therefore, the cell introduction efficiency may decrease.

When the target cell is *E. coli* bacterium, the homologous region preferably has a length of at least 50 bp or more, and when the length of the homologous region is less than 50 bp, the efficiency of homologous recombination may decrease. The length of the homologous region may be designed to be 100 bp or more or 500 bp or more in order to facilitate distinction of success experimentally.

The homologous region may be designed by appropriately selecting it according to a target position to which a target gene is to be introduced by a person skilled in the art, and in one embodiment, the homologous region may be the nucleic acid sequence of SEQ ID NOs: 18 to 31.

The homologous region (or homologous arm) attached to the 5' end of the target gene in the homologous region comprises a nucleic acid sequence in which the PAM (protospacer adjacent motif) sequence is substituted with other sequence. The PAM sequence is known to play a role of designating a location which Cas9 protein (Cas restriction enzyme) cleaves, and generally, it has the sequence of NGG. Then, each "N" base of the PAM sequence means a "A", "T", "G" or "C" base. In the present description, the PAM sequence may mean "NNGG", further comprising one base at the 5' end of the generally known "NGG" sequence.

The nucleic acid sequence substituting the PAM sequence may be used without limitation as long as it is not the sequence of 'NNGG' within the range of the purpose to prevent from being recognized specifically to Cas9, and for example, the NNGG nucleic acid sequence may be substituted with a nucleic acid sequence of NNAA, NNAT, NNAG, NNAC, NNTA, NNTT, NNTG, NNTC, NNCA, NNCT, NNCG, NNCC, NNGA, NNGT, or NNGC.

When the homologous region in which the PAM sequence is not substituted is attached to the 5' end of the target gene, there is a risk that Cas9 protein re-recognizes the corresponding site and cleaves it again while repeatedly introducing the target gene.

In the present description, the preparation method of a transformant comprises the following steps:

(1) introducing the composition and/or system provided by the present invention into a target cell;
(2) inserting a target gene to a target site of the target cell, by expressing Cas9 and recombinase in the target cell; and
(3) removing a G recombinant vector by culturing a cell in which the target gene is inserted into the target site at a temperature of 36 degrees Celsius or more.

The transformant prepared by the method may be one in which a target gene is inserted (multiple insertion or multiple introduction) into a plurality of target sites present on genome. The target gene inserted into each target site may be same and/or different from each other.

The preparation method of a transformant provided by the present invention comprises (1) introducing the composition and/or system provided by the present invention into a target cell.

Specific contents for the composition and/or system are as described above.

In the step (1), the common recombinant vector and variable recombinant vector set may be introduced simultaneously and/or sequentially, and they may be introduced by freely selecting a method known in the art within the range of the purpose of external vector introduction.

In the present description, the preparation method of a transformant comprises (2) inserting the target gene at the target site of the target cell, by expressing Cas9 and recombinase in the target cell.

The target site of the target cell is determined by gRNA expressed in the G recombinant vector introduced into the target cell, and Cas9 cleaves (for example, double strand break) the PAM sequence (NNGG) at the position designated by the corresponding gRNA.

The expressing Cas9 and/or recombinase in the target cell, may be performed by inducing using an inducible promoter. In one embodiment, the inducible promoter may be an inducible promoter by arabinose.

When the Cas9 and/or recombinase are always expressed, the metabolic burden of the target cell may increase, and a risk of damage to unintended genome site may increase.

In the present description, the preparation method of a transformant, comprises (3) removing a G recombinant vector by culturing a cell in which the target gene is inserted into the target site at a temperature of 36 degrees Celsius or more.

The removal of the G recombinant vector may be performed by the aforementioned temperature sensitive origin (ts origin). The culturing temperature may be appropriately selected according to the type of the temperature sensitive origin, and may be 36 degrees Celsius (hereinafter, same) or more, 37 degrees or more, 39 degrees or more or 41 degrees or more, but not limited thereto.

In the present description, the preparation method of a transformant, may further comprise the following steps, after the removing the G recombinant vector:

(i) introducing a variable recombinant vector set specific to a new target site other than a site which is present on genome of the transformant and the target gene is inserted into, into the transformant;

(ii) inserting the target gene into the new target site, by expressing Cas9 and recombinase in the transformant in which the variable recombinant vector set is introduced; and (iii) removing a G recombinant vector by culturing the transformant in which the target gene is inserted into the new target site at a temperature of 36 degrees Celsius or more.

The step (i) to step (iii) may be repeated as many as the number of target sites present on genome of the target cell. The gRNA and/or homologous region in the variable recombinant vector set may be substituted and used for each target site.

There are advantages in that the target gene may be inserted into a plurality of target sites by the repeating step, and a large target gene with an overall length of 9 kb or more or 10 kb or more of the introduced target gene can be quickly and simply introduced into the genome of the target cell.

The present invention also provides a transformant prepared by the method.

The overall length of the target gene inserted in the transformant may be 1 kb or more, 5 kb or more, 10 kb or more, 1 to 30 kb, 1 to 15 kb, 1 to 10 kb, 5 to 30 kb, 5 to 15 kb, 5 to 10 kb, 10 to 30 kb, or 10 to 15 kb, but not limited thereto.

The 3-HP producing gene of *E. coli* bacterium in which a foreign 3-hydroxypropionic acid (3-hydroxypropionate, 3-HP) producing gene is inserted into genomic DNA provided in the present description may be 1 copy number or more and 100 copy numbers or less, 2 copy numbers or more and 100 copy numbers or less, 3 copy numbers or more and 100 copy numbers or less, 4 copy numbers or more and 100 copy numbers or less, 5 copy numbers or more and 100 copy numbers or less, 6 copy numbers or more and 100 copy numbers or less, 7 copy numbers or more and 100 copy numbers or less, 10 copy numbers or more and 100 copy numbers or less, 12 copy numbers or more and 100 copy numbers or less, 1 copy number or more and 50 copy numbers or less, 2 copy numbers or more and 50 copy numbers or less, 3 copy numbers or more and 50 copy numbers or less, 4 copy numbers or more and 50 copy numbers or less, 5 copy numbers or more and 50 copy numbers or less, 6 copy numbers or more and 50 copy numbers or less, 7 copy numbers or more and 50 copy numbers or less, 10 copy numbers or more and 50 copy numbers or less, 12 copy numbers or more and 50 copy numbers or less, 1 copy number or more and 30 copy numbers or less, 2 copy numbers or more and 30 copy numbers or less, 3 copy numbers or more and 30 copy numbers or less, 4 copy numbers or more and 30 copy numbers or less, 5 copy numbers or more and 30 copy numbers or less, 6 copy numbers or more and 30 copy numbers or less, 7 copy numbers or more and 30 copy numbers or less, 10 copy numbers or more and 30 copy numbers or less, 12 copy numbers or more and 30 copy numbers or less, 1 copy number or more and 20 copy numbers or less, 2 copy numbers or more and 20 copy numbers or less, 3 copy numbers or more and 20 copy numbers or less, 4 copy numbers or more and 20 copy numbers or less, 5 copy numbers or more and 20 copy numbers or less, 6 copy numbers or more and 20 copy numbers or less, 7 copy numbers or more and 20 copy numbers or less, 10 copy numbers or more and 20 copy numbers or less, 12 copy numbers or more and 20 copy numbers or less, 1 copy number or more and 15 copy numbers or less, 2 copy numbers or more and 15 copy numbers or less, 3 copy numbers or more and 15 copy numbers or less, 4 copy numbers or more and 15 copy numbers or less, 5 copy numbers or more and 15 copy numbers or less, 6 copy numbers or more and 15 copy numbers or less, 7 copy numbers or more and 15 copy numbers or less, 10 copy numbers or more and 15 copy numbers or less, 12 copy numbers or more and 15 copy numbers or less, 1 copy number or more and 12 copy numbers or less, 2 copy numbers or more and 12 copy numbers or less, 3 copy numbers or more and 12 copy numbers or less, 4 copy numbers or more and 12 copy numbers or less, 5 copy numbers or more and 12 copy numbers or less, 6 copy numbers or more and 12 copy numbers or less, 7 copy numbers or more and 12 copy numbers or less, 10 copy numbers or more and 12 copy numbers or less, 1 copy number or more and 10 copy numbers or less, 2 copy numbers or more and 10 copy numbers or less, 3 copy numbers or more and 10 copy numbers or less, 4 copy numbers or more and 10 copy numbers or less, 5 copy numbers or more and 10 copy numbers or less, 6 copy numbers or more and 10 copy numbers or less, 7 copy numbers or more and 10 copy numbers or less, 1 copy number or more and 8 copy numbers or less, 2 copy numbers or more and 8 copy numbers or less, 3 copy numbers or more and 8 copy numbers or less, 4 copy numbers or more and 8 copy numbers or less, 5 copy numbers or more and 8 copy numbers or less, 6 copy numbers or more and 8 copy numbers or less, 7 copy numbers or more and 8 copy numbers or less, 1 copy number or more and 7 copy numbers or less, 2 copy numbers or more and 7 copy numbers or less, 3 copy numbers or more and 7 copy numbers or less, 4 copy numbers or more and 7 copy numbers or less, 5 copy numbers or more and 7 copy numbers or less, 6 copy numbers or more and 7 copy numbers or less, 1 copy number or more and 6 copy numbers or less, 2 copy numbers or more and 6 copy numbers or less, 3 copy numbers or more and 6 copy numbers or less, 4 copy numbers or more and 6 copy numbers or less or 5 copy numbers or more and 6 copy numbers or less, and for example, may be 5 copy numbers, 6 copy numbers, 7 copy numbers, 8 copy numbers, 9 copy numbers, 10 copy numbers, 11 copy numbers or 12 copy numbers, but not limited thereto.

In one embodiment, the microorganism (for example, *E. coli* bacterium) may be a strain which has 3-HP producing ability or is genetically engineered to have 3-HP producing ability. The production of 3-HP includes that produced in the strain, that produced in a cell and secreted outside the cell, or a combination thereof.

In the present description, "glycerol dehydratase" is enzyme that catalyzes a chemical reaction, and belongs to the family of lyase, in particular, hydrolase, that cleaves carbon-oxygen bonds, and participates in glycerol lipid metabolism, and uses a cofactor, cobalamin. The enzyme may be one encoded by dhaB (GenBank accession no. U30903.1) gene, but not limited thereto.

The dhaB gene is derived from *Klebsiella pneumonia*, and the gene encoding glycerol dehydratase may comprise genes encoding dhaB1, dhaB2 and/or dhaB3, but not limited thereto. The glycerol dehydratase protein and gene encoding this may comprise a mutation of the gene and/or amino acid sequence within the range of maintaining the enzymatic activity of degrading glycerol into-hydroxypropanal (3-HPA) and water ($H_2O$).

In the present description, "aldehyde dehydrogenase" is enzyme that catalyzes oxidation of aldehyde. The enzyme may convert aldehyde (R—C(═O)—H) into carboxylic acid (R—C(═O)—O—H). The enzyme may be encoded by aldH gene, and the gene may be aldH (GenBank Accession no. U00096.3; EaldH) gene derived from *Escherichia coli* or *E. coli* bacterium K12 MG1655 18-3 cell line, puuC gene derived from *Klebsiella pneumonia* (*K. pneumonia*) and/or KGSADH gene derived from Azospirillum brasilense, but not limited thereto. The aldehyde dehydrogenase protein and gene encoding this may comprise a mutation of the gene and/or amino acid sequence within the range of maintaining activity to produce 3-HP from 3-HPA.

In the present description, "glycerol dehydratase reactivase" acts to maintain the activity of the catalyst during the catalyst reaction of glycerol dehydratase. The enzyme may be encoded by gdrAB gene, and may be derived from *Klebsiella pneumonia.*

In the present description, "adenosyltransferase" plays a role of improving vitamin B1 reuse, and may be encoded by gene btuR (GenBank: AAA23530.1), and this may be derived from *Escherichia coli.*

In the present description, "yghD" is a gene encoding alcohol dehydrogenase, and encodes enzyme which converts 3-hydroxypropanal into 1,3-PDO when glycerol is degraded into 3-hydroxypropanal and water by glycerol dehydratase.

In the present description, "glpK" may be a gene encoding glycerol kinase.

In the present description, "ldhA" may be a gene encoding lactate dehydrogenase.

In the present description, "gldA" may be a gene encoding glycerol dehydrogenase.

In the present description, "ack-pta" may be a gene encoding acetate kinase-phosphate acetyltransferase.

In the present description, "mgsA" may be a gene encoding methylglyoxal synthase.

In the present description, "poxB" may be a gene encoding pyruvate dehydrogenase.

In the present description, "nfrA" may be a gene encoding bacteriophage adsorption protein A.

In the present description, "vector" refers to any vehicle for cloning and/or transition of a base into a host cell. The vector may be a replicon capable of bringing about replication of fragments bound by binding other DNA fragments. "Replicon" may mean any genetic unit (for example, plasmid, phage, cosmid, chromosome, virus), which functions as a self-unit of DNA replication in vivo, i.e. capable of replication by its own regulation. In the present invention, the vector is not particularly limited as long as it can replicate in a host, and any vector known in the art may be used. The vector used for construction of the recombinant vector may be a plasmid, cosmid, virus and/or bacteriophage in a natural state or recombinant state. For example, as the phage vector or cosmid vector, pWE15, M13, λEMBL3, λEMBL4, λFIXII, λDASHII, λZAPII, λgt10, λgt11, Charon4A, and/or Charon21A, and the like may be used, and as the plasmid vector, pDZ vector, pBR-based, pUC-based, pBluescriptII-based, pGEM-based, pTZ-based, pCL-based, and/or pET-based, and the like may be used. The usable vector is not particularly limited, and a known expression vector may be used. In one embodiment, the vector may be one such that a gene transferred by being inserted into the vector is irreversibly fused into genome of a host cell so that gene expression is stably maintained for a long time in the cell. This vector, may comprise a transcription and translation expression regulatory sequence which allows the corresponding gene can be expressed in the selected host. As the expression regulatory sequence, any operator sequence for regulating transcription and/or a sequence regulating termination of transcription and translation may be comprised. In one embodiment, an initiation codon and a stop codon may be generally considered as a part of a nucleic acid sequence encoding a target protein, and they should exhibit action in a subject when a genetic construct is administered and may be in frame with a coding sequence. In addition, in case of the replicable expression vector, it may comprise a replication origin. In addition, it may appropriately comprise an enhancer, an untranslated region at the 3' end of the targeted gene, a selection marker (for example, antibiotic-resistant marker) and/or a replicable unit and the like. The vector may be self-replicating or may be integrated into host genomic DNA.

According to one embodiment, each element in the vector should be operably linked, and the linkage of these element sequences may be performed at a convenient restriction enzyme site by ligation (linkage), and when such a site is not present, it may be performed using a synthetic oligonucleotide adaptor or linker according to a common method.

In the present description, "transduction" refers to a phenomenon in which bacterial DNA is transferred to other bacteria through a bacteriophage, and is one of methods of horizontal gene transfer (HGT). Such transducible bacteriophage is called "transduction particle" or "transduction phage", and a cell that has received DNA from other bacteria is called "transductant".

In the present description, "transformation" is to produce a gene into a host cell so that is can be expressed in a host cell, and when the transformed gene can be expressed in the host cell, anything inserted in chromosome of the host cell or positioned outside the chromosome may be included without limitation. In addition, the gene includes DNA and/or RNA encoding a target protein. As long as the gene can be introduced and expressed into a host microorganism, the introduced form is not limited. For example, the gene may be introduced into a host microorganism in the form of an expression cassette, which is a gene construct including all elements necessary for self-expression. The expression cassette may commonly comprise expression regulatory elements such as a promoter, a transcription termination signal, a ribosome binding site and/or a translation termination signal and the like, which are operably linked to the gene. The expression cassette may be in the form of an expression vector capable of self-replication. In addition, the gene may be introduced into a host cell in its own form and be operably linked to a sequence required for expression in the host cell.

In the present description, the method for transforming includes anything as long as it is a method of introducing a gene into a cell, and may be performed by selecting a suitable standard technique as known in the art. For example, electroporation, calcium phosphate (CaPO4) precipitation, calcium chloride (CaCl2)) precipitation, microinjection, retroviral infection, polyethylene glycol (PEG) method, DEAE-dextran method, cationic liposome method and/or lithium acetate-DMSO method may be used, but not limited thereto.

In the method for determining 3-HP producing ability of the 3-HP producing gene inserted into genomic DNA of the microorganism (for example, *E. coli* bacterium), comprising culturing a microorganism (for example, *E. coli* bacterium), the culturing may comprise the first culturing step and/or the first culturing step and the second culturing step, but not limited thereto.

The culturing a microorganism (for example, *E. coli* bacterium), may comprise the first culturing step which is culturing in a medium comprising glucose and/or sucrose as a carbon source; and the second culturing step which is culturing in a medium comprising glycerol as a carbon source, but not limited thereto.

The medium comprising glucose and/or sucrose as a carbon source may be LB medium, and the medium comprising glycerol as a carbon source may be M9 medium, but not limited thereto.

The culturing may be made according to an appropriate medium and culture conditions known in the art, and it should meet requirements of a specific strain in an appropriate manner, and may be appropriately modified by a person skilled in the art.

The culture method may comprise for example, batch culture, continuous culture, fed-batch culture, or a combination thereof, but not limited thereto.

The fed-batch culture may be carried out using a 5 L fermenter (Working volume 2 L), and may be carried out by performing high-concentration cell culture, but not limited thereto.

According to one embodiment, the medium may comprise various carbon sources, nitrogen sources and trace element components, and the recombinant cell may be cultured in a common medium containing a proper carbon source, a nitrogen source, an amino acid, a vitamin and the like while adjusting temperature and/or pH and the like. The carbon source that may be used includes sugars and carbohydrates such as glucose, sucrose, lactose, fructose, maltose, starch and/or cellulose, oils and fats such as soybean oil, sunflower oil, castor oil and/or coconut oil and the like, fatty acids such as palmitic acid, stearic acid, and/or linolenic acid, alcohols such as glycerol and/or ethanol, and organic acid such as acetic acid. These materials may be used individually or as a mixture, but not limited thereto. As the nitrogen that can be used, peptone, yeast extract, meat juice, malt extract, corn steep liquor, soybean wheat and urea or an inorganic compound, for example, ammonium sulfate, ammonium chloride, ammonium phosphate, ammonium carbonate and ammonium nitrate may be comprised. The nitrogen source may also be used individually or as a mixture, but not limited thereto. The phosphorus source that can be used may comprise potassium dihydrogen phosphate or dipotassium hydrogen phosphate or a sodium-containing salt corresponding thereto, but not limited thereto. Furthermore, the medium may contain a metal salt such as magnesium sulfate or iron sulfate necessary for growth, but not limited thereto. In addition, an essential growth substance such as amino acids and vitamins may be comprised. Moreover, precursors suitable for the medium may be used. The medium or individual components may be added batchwise or continuously by an appropriate method to the culture solution during the culturing process, but not limited thereto.

According to one embodiment, by adding a compound such as ammonium hydroxide, potassium hydroxide, ammonia, phosphoric acid and sulfuric acid to microbial culture solution by an appropriate method during culturing, pH of the culture solution may be adjusted. In addition, bubble generation may be inhibited using an antifoaming agent such as fatty acid polyglycol ester during culturing. Additionally, in order to maintain the aerobic state of the culture solution, oxygen or oxygen-containing gas (e.g., air) may be injected into the culture solution. The temperature of the culture solution may be 20° C. to 45° C., 25° C. to 40° C. or 30° C. to 37° C., and for example, may be 37° C. The culture period may be continued until a useful substance (for example, 3-HP) is obtained in a desired yield, and for example, may be 3 to 60 hours, 3 to 48 hours, 3 to 36 hours, 3 to 28 hours, 6 to 60 hours, 6 to 48 hours, 6 to 36 hours, 6 to 28 hours, 12 to 60 hours, 12 to 48 hours, 12 to 36 hours, 12 to 28 hours, 20 to 60 hours, 20 to 48 hours, 20 to 36 hours or 20 to 28 hours, and for example, may be 24 hours, but not limited thereto.

The separating and/or recovering 3-HP in the cultured microorganism (or recombinant cell) and/or culture medium may be collecting a targeted substance (for example, 3-HP) form the medium, culture solution or microorganism using an appropriate method known in the art according to the culture method. For example, a method of centrifugation, filtration, extraction, spraying, drying, evaporation, precipitation, crystallization, electrophoresis, fractional dissolution (for example, ammonium sulfate precipitation) and/or chromatography (for example, ion exchange, affinity, hydrophobic, liquid and size exclusion) and the like may be used, but not limited thereto. The culture medium may mean a medium in which a microorganism (or recombinant cell) is cultured.

In one embodiment, the method for producing 3-HP may additionally comprise purifying 3-HP before, at the same time of, or after the separating and/or recovering.

Advantageous Effects

In the present description, the microorganism and/or *E. coli* bacterium in which a foreign 3-hydroxypropionic acid (3-hydroxypropionate, 3-HP) is inserted into genomic DNA has 3-HP producing ability, and a composition for determining 3-HP producing ability of the 3-HP producing gene inserted into the genomic DNA comprising the microorganism and/or *E. coli* bacterium is provided. In addition, a method for determining 3-HP producing ability of the 3-HP producing gene inserted into the microorganism and/or *E. coli* bacterium genomic DNA is provided.

BRIEF DESCRIPTION OF THE DRAWINGS

FIG. 1 is a cleavage map of the common recombinant vector comprising Cas9 gene and recombinase.

FIG. 2 shows the homology arm region connected before and after the insertion site to the 5' and 3' ends of the target gene comprised in the D recombinant DNA.

FIG. 3 shows the cassette recombinant vector comprising 4 kinds of target genes (inserted genes).

FIG. 4 shows the 3-HP producing gene plasmid vector, pCDF_J23101_dhaB_gdrAB_J23100_aldH_btuR vector.

FIG. 5 shows the 3-HP producing pRSF plasmid vector based on the pRSFDuet-1 vector.

MODE FOR INVENTION

Hereinafter, the present invention will be described in detail by examples. However, the following examples illustrates the present invention only, but the present invention is not limited by the following examples.

Unless otherwise mentioned in the present description, all temperatures are based on degrees Celsius, and nucleic acid sequences are described in the direction from the 5' end to the 3' end unless otherwise specified.

Example 1. Plasmid Design for Strain Recombination

1-1. Preparation of Common Recombinant Vector (Comprising Cas9 and Recombinase)

In the present example, a common recombinant vector comprising Cas9 gene and recombinase was prepared.

More specifically, under araBAD promoter induced RSF origin, arabinose, Cas9 gene (SEQ ID NO: 1) and recombinase (RED recombinase; SEQ ID NO: 2) were inserted into an araC gene and RED recombinase gene expression vector that regulates transcription of Cas9, to prepare a common recombinant vector, and the specific information was shown in Table 1 below.

The cleavage map of the common recombinant vector was shown in FIG. 1. The common recombinant vector is always maintained in a recombinant cell without an additional gene insertion process after being inserted once at the time of the first gene insertion, and performs a function to edit genome according to the kind of gRNA to be introduced and homolog region.

TABLE 1

| Name | Sequence (5'→3') | SEQ ID NO |
|---|---|---|
| Cas9 gene | atggataagaaatactcaataggcttagatatcggcacaaatagcgtcggatgggcggtgatcactgat<br>gaatataaggttccgtctaaaaagttcaaggttctgggaaatacagaccgccacagtatcaaaaaaaa<br>tcttataggggctcttttatttgacagtggagagacagcggaagcgactcgtctcaaacggacagctcgt<br>agaaggtatacacgtcggaagaatcgtatttgttatctacaggagatttttcaaatgagatggcgaaa<br>gtagatgatagtttctttcatcgacttgaagagtcttttttggtggaagaagacaagaagcatgaacgtc<br>atcctattttggaaatatagtagatgaagttgcttatcatgagaaatatccaactatctatcatctgcga<br>aaaaaattggtagattctactgataaagcggatttgcgcttaatctatttggccttagcgcatatgattaa<br>gtttcgtggtcatttttgattgagggagatttaaatcctgataatagtgatgtggacaaactatttatcca<br>gttggtacaaacctacaatcaattatttgaagaaaaccctattaacgcaagtggagtagatgctaaagc<br>gattctttctgcacgattgagtaaatcaagacgattagaaaatctcattgctcagctccccggtgagaag<br>aaaaatggcttatttgggaatctcattgctttgtcattgggtttgacccctaattttaaatcaaattttgatt<br>tggcagaagatgctaaattacagctttcaaaagatacttacgatgatgatttagataatttattggcgca<br>aattggagatcaatatgctgatttgtttttggcagctaagaatttatcagatgctattttactttcagatat<br>cctaagagtaaatactgaaataactaaggctcccctatcagcttcaatgattaaacgctacgatgaaca<br>tcatcaagacttgactcttttaaaagctttagttcgacaacaacttccagaaaagtataaagaaatctttt<br>ttgatcaatcaaaaaacggatatgcaggttatattgatgggggagctagccaagaagaattttataaat<br>ttatcaaaccaattttagaaaaaatggatggtactgaggaattattggtgaaactaaatcgtgaagattt<br>gctgcgcaagcaacggacctttgacaacggctctattccccatcaaattcacttgggtgagctgcatgct<br>attttgagaagacaagaagacttttatccattttaaaagacaatcgtgagaagattgaaaaaatcttg<br>acttttcgaattccttattatgttggtccattggcgcgtggcaatagtcgttttgcatggatgactcggaag<br>tctgaagaaacaattaccccatggaattttgaagaagttgtcgataaaggtgcttcagctcaatcattta<br>ttgaacgcatgacaaactttgataaaaatcttccaaatgaaaaagtactaccaaaacatagtttgcttta<br>tgagtattttacggtttataacgaattgacaaaggtcaaatatgttactgaaggaatgcgaaaaccagc<br>atttctttcaggtgaacagaagaaagccattgttgatttactcttcaaaacaaatcgaaaagtaaccgtt<br>aagcaattaaaagaagattatttcaaaaaaatagaatgttttgatagtgttgaaatttcaggagttgaa<br>gatagatttaatgcttcattaggtacctaccatgatttgctaaaaattattaaagataaagatttttttggat<br>aatgaagaaaatgaagatatcttagaggatattgttttaacattgaccttatttgaagatagggagatg<br>attgaggaaagacttaaaacatatgctcacctctttgatgataaggtgatgaaacagcttaaacgtcgc<br>cgttatactggttggggacgtttgtctcgaaaattgattaatggtattagggataagcaatctggcaaaa<br>caatattagatttttttgaaatcagatggttttgccaatcgcaattttatgcagctgatccatgatgatagtt<br>tgacatttaaagaagacattcaaaaagcacaagtgtctggacaaggcgatagtttacatgaacatattg<br>caaatttagctggtagccctgctattaaaaaaggtattttacagactgtaaaagttgttgatgaattggtc<br>aaagtaatggggcggcataagccagaaaatatcgttattgaaatggcacgtgaaaatcagacaactca<br>aaagggccagaaaaattcgcgagagcgtatgaaacgaatcgaagaaggtatcaaagaattaggaag<br>tcagattcttaaagagcatcctgttgaaaatactcaattgcaaaatgaaaagctctatctctattatctcc | 1 |

TABLE 1-continued

| Name | Sequence (5'→3') | SEQ ID NO |
|---|---|---|
| | aaaatggaagagacatgtatgtggaccaagaattagatattaatcgtttaagtgattatgatgtcgatc<br>acattgttccacaaagtttccttaaagacgattcaatagacaataaggtcttaacgcgttctgataaaaa<br>tcgtggtaaatcggataacgttccaagtgaagaagtagtcaaaaagatgaaaaactattggagacaac<br>ttctaaacgccaagttaatcactcaacgtaagtttgataatttaacgaaagctgaacgtggaggtttgag<br>tgaacttgataaagctggttttatcaaacgccaattggttgaaactcgccaaatcactaagcatgtggca<br>caaattttggatagtcgcatgaatactaaatacgatgaaaatgataaacttattcgagaggttaaagtg<br>attaccttaaaatctaaattagtttctgacttccgaaaagatttccaattctataaagtacgtgagattaa<br>caattaccatcatgcccatgatgcgtatctaaatgccgtcgttggaactgctttgattaagaaatatcca<br>aaacttgaatcggagtttgtctatggtgattataaagtttatgatgttcgtaaaatgattgctaagtctga<br>gcaagaaataggcaaagcaaccgcaaaatatttcttttactctaatatcatgaacttcttcaaaacaga<br>aattacacttgcaaatggagagattcgcaaacgccctctaatcgaaactaatggggaaactggagaaa<br>ttgtctgggataaagggcgagattttgccacagtgcgcaaagtattgtccatgccccaagtcaatattgt<br>caagaaaacagaagtacagacaggcggattctccaaggagtcaattttaccaaaaagaaattcggac<br>aagcttattgctcgtaaaaaagactgggatccaaaaaaatatggtggttttgatagtccaacggtagctt<br>attcagtcctagtggttgctaaggtggaaaaagggaaatcgaagaagttaaaatccgttaaagagtta<br>ctagggatcacaattatggaaagaagttcctttgaaaaaaatccgattgactttttagaagctaaagga<br>tataaggaagttaaaaaagacttaatcattaaactacctaaatatagtctttttgagttagaaaacggtc<br>gtaaacggatgctggctagtgccggagaattacaaaaaggaaatgagctggctctgccaagcaaatat<br>gtgaatttttatatttagctagtcattatgaaaagttgaagggtagtccagaagataacgaacaaaaa<br>caattgtttgtggagcagcataagcattatttagatgagattattgagcaaatcagtgaattttctaagcg<br>tgttattttagcagatgccaatttagataaagttcttagtgcatataacaaacatagagacaaaccaata<br>cgtgaacaagcagaaaatattattcatttatttacgttgacgaatcttggagctcccgctgcttttaaata<br>ttttgatacaacaattgatcgtaaacgatatacgtctacaaaagaagttttagatgccactcttatccatc<br>aatccatcactggtctttatgaaacacgcattgatttgagtcagctaggaggtgactga | |
| RED recomgbinase gene | atggatattaatactgaaactgagatcaagcaaaagcattcactaaccccctttcctgttttcctaatcag<br>cccggcatttcgcgggcgatattttcacagctatttcaggagttcagccatgaacgcttattacattcagg<br>atcgtcttgaggctcagagctgggcgcgtcactaccagcagctcgcccgtgaagagaaagaggcagaa<br>ctggcagacgacatggaaaaaggcctgccccagcacctgtttgaatcgctatgcatcgatcatttgcaa<br>cgccacggggccagcaaaaaatccattacccgtgcgtttgatgacgatgttgagtttcaggagcgcatg<br>gcagaacacatccggtacatggttgaaaccattgctcaccaccaggttgatattgattcagaggtataa<br>aacgaatgagtactgcactcgcaacgctggctgggaagctggctgaacgtgtcggcatggattctgtcg<br>acccacaggaactgatcaccactcttcgccagacggcatttaaaggtgatgccagcgatgcgcagttca<br>tcgcattactgatcgttgccaaccagtacggccttaatccgtggacgaaagaaatttacgcctttcctgat<br>aagcagaatggcatcgttccggtggtgggcgttgatggctggtcccgcatcatcaatgaaaaccagcag<br>tttgatggcatggactttgagcaggacaatgaatcctgtacatgccggatttaccgcaaggaccgtaatc<br>atccgatctgcgttaccgaatggatggatgaatgccgccgcgaaccattcaaaactcgcgaaggcaga<br>gaaatcacggggccgtggcagtcgcatcccaaacggatgttacgtcataaagccatgattcagtgtgcc<br>cgtctggccttcggatttgctggtatctatgacaaggatgaagccgagcgcattgtcgaaaatactgcat<br>acactgcagaacgtcagccggaacgcgacatcactccggttaacgatgaaaccatgcaggagattaac<br>actctgctgatcgccctggataaaacatgggatgacgacttattgccgctctgttcccagatatttcgccg<br>cgacattcgtgcatcgtcagaactgacacaggccgaagcagtaaaagctcttggattcctgaaacaga<br>aagccgcagagcagaaggtggcagcatgacaccggacattatcctgcagcgtaccgggatcgatgtg<br>agagctgtcgaacaggggatgatgcgtggcacaaattacggctcggcgtcatcaccgcttcagaagtt<br>cacaacgtgatagcaaaaccccgctccggaaagaagtggcctgacatgaaaatgtcctacttccacac<br>cctgcttgctgaggtttgcaccggtgtggctccggaagttaacgctaaagcactggcctggggaaaaca<br>gtacgagaacgacgccagaaccctgtttgaattcacttccggcgtgaatgttactgaatccccgatcatc<br>tatcgcgacgaaagtatgcgtaccgcctgctctcccgatggtttatgcagtgacggcaacggccttgaac<br>tgaaatgcccgtttacctcccgggatttcatgaagttccggctcggtggtttcgaggccataaagtcagct<br>tacatggcccaggtgcagtacagcatgtgggtgacgcgaaaaaatgcctggtactttgccaactatgac<br>ccgcgtatgaagcgtgaaggcctgcattatgtcgtgattgagcgggatgaaaagtacatggcgagtttt<br>gacgagatcgtgccggagttcatcgaaaaaatggacgaggcactggctgaaattggttttgtatttggg<br>gagcaatggcgatga | 2 |

1-2 G Recombinant Vector (Comprising Guide RNA and Ts Origin)

Under temperature sensitive pSC101 origin, ampicillin antibiotic resistant gene and J23100 promoter, an expression vector comprising sgRNA designating an integration site and sgRNA scaffold (sequence that associates with Cas9) of CRISPR-Cas9 system of *Streptococcus* pyrogenes (*S. pyogenes*) was prepared, and named as G (Guide RNA-containing) recombinant vector.

The sgRNA may be prepared by a method known in the art depending on the insertion target site, and the nucleic acid sequence of the gene encoding the sgRNA used in the present invention was shown in Table 2 below.

TABLE 2

| Target | gRNA sequence (5'→3') | Accession Number | SEQ ID NO | Name of the sequence |
|---|---|---|---|---|
| ldhA | GCACGTTGTGGCAGGCAGAC | BAA14990.1 | 3 | ldhA_gRNA1 |
| | TAACGTCTGATTCAGAGAAC | (GenBank) | 4 | ldhA_gRNA2 |
| | AACGTCTGATTCAGAGAACA | | 5 | ldhA_gRNA3 |
| yqhD | ACTTTCCTGCTGGCGGTTGG | BAE77068.1 | 6 | yqhD_gRNA1 |
| | CACCAAATTTATCGCCGCAG | (GenBank) | 7 | yqhD_gRNA2 |

TABLE 2-continued

| Target | gRNA sequence (5'→3') | Accession Number | SEQ ID NO | Name of the sequence |
|---|---|---|---|---|
| glpK | ATTGTCTGGGAAAAAGAAAC | BAE77384.1 | 8 | glpK_gRNA1 |
| | CGTCGTTCTTCCGAAGTATA | (GenBank) | 9 | glpK_gRNA2 |
| gldA | ATCGCGGAGACTGCGCAGTG | AAC76927.2 | 10 | gldA_gRNA1 |
| | CCTCGATACTGCCAAAGCAC | (GenBank) | 11 | gldA_gRNA2 |
| mgsA | CGAGATAACGCTGATAATCG | CAA72119.1 | 12 | mgsA_gRNA1 |
| | CGCAGCAAGGCTTTCACGTC | (GenBank) | 13 | mgsA_gRNA2 |
| poxB | CAGTGCATGGTTGCCCCTTC | CAA27725.1 | 14 | poxB_gRNA1 |
| | GTACTTGTGGGATCTGCTCC | (GenBank) | 15 | poxB_gRNA2 |
| nfrA | CGCATGCAGCCACCAGTAGA | AAC36849.1 | 16 | nfrA_gRNA1 |
| | CCAGTCGCGCCATTAAAGTC | (GenBank) | 17 | nfrA_gRNA2 |

1-3. D Recombinant DNA (Comprising Homology Region and Target Gene)

D (Donor) recombinant DNA comprising a target gene (donor or insert) to be introduced into genome was prepared as follows.

As the target gene, dhaB, gdrAB, aldH and btuR parts of the pCDF_J23101_dhaB_gdrAB_J23100_aldH_btuR vector of Korean Patent Publication No. 10-2020-0051375 were used, and homology arm regions with a length of 1 kb were connected before and after the insertion site at the 5' and 3' ends of the target gene, respectively. Then, the PAM sequence (NNGG) comprised in the homology arm in the 5' direction (beginning part of foreign target gene operon) was substituted with CAAA to prepare a 3-HP producing gene cassette recombinant vector (See FIG. 3). In the PAM sequence, the N base means an A base, a T base, a C base or a G base.

Specifically, by treating xbaI and paI restriction enzymes (Thermo Scientific) to the pCDF_J23101sdhaB_gdrABcJ23act_aldH_btuR vector, fragments were prepared, and PCR was performed on the genomic DNA of the *E. coli* W3110 strain (purchased from KCRC) with primers of Table 3 below, and upstream and downstream fragments of the homology arm were prepared, and the two fragments were mixed by In-fusion (TAKARA) reaction to prepare a 3-HP producing gene cassette recombinant vector.

TABLE 3

| homology arm primer | homology arm sequence (5'→3') | SEQ ID NO |
|---|---|---|
| ldhA_upstream_For | actgaaccgctctaggcgattgggatgtgtgcattacc | 48 |
| ldhA_upstream_Rev | tagctgtaaatctagatctctctgcactgcccgc | 49 |
| ldhA_downstream_For | tactagcgcagcttaagctcaaagccaaaggactcg | 50 |
| ldhA_downstream_Rev | cagcagcctaggttaacgatcaattgcccgctattttcc | 51 |
| yqhD_upstream_For | actgaaccgctctagggcggagttaatcccgctg | 52 |
| yqhD_upstream_Rev | tagctgtaaatctagcactttctgttcgcgaaccagtttc | 53 |
| yqhD_downstream_For | tactagcgcagcttagaacagtatgttaccaaaccggttg | 54 |
| yqhD_downstream_Rev | cagcagcctaggttaagggctttgccgacacct | 55 |
| glpK_upstream_For | tactagcgcagcttaacctatggcactggctgct | 56 |
| glpK_upstream_Rev | tagctgtaaatctaggtcatattacagcgaagctttttgt | 57 |
| glpK_downstream_For | tactagcgcagcttaaagcgtttatgccgcatccg | 58 |
| glpK_downstream_Rev | cagcagcctaggttatcttcgttgtcgcctttgacg | 59 |
| gldA_upstream_For | actgaaccgctctagcatgcacgaagaattccgtaac | 60 |
| gldA_upstream_Rev | tagctgtaaatctagaaacctaaaacaaatttgtcaccc | 61 |
| gldA_downstream_For | tactagcgcagcttagaagcggcatgtgcagaagg | 62 |
| gldA_downstream_Rev | cagcagcctaggttatctgaaaccaccccaatatgtgc | 63 |
| mgsA_upstream_For | actgaaccgctctaggattgtgattctggagaaaggtcgc | 64 |
| mgsA_upstream_Rev | tagctgtaaatctagcggaccgtctgaagtaatattgc | 65 |

TABLE 3-continued

| homology arm primer | homology arm sequence (5'→3') | SEQ ID NO |
|---|---|---|
| mgsA_downstream_For | tactagcgcagcttatccgcgcaggtaaagtgc | 66 |
| mgsA_downstream_Rev | cagcagcctaggttacgaatgaatgagagcaaaagcggg | 67 |
| poxB_upstream_For | actgaaccgctctagcggcattaaagatgcgcgca | 68 |
| poxB_upstream_Rev | tagctgtaaatctagacaacagcgtgctgggct | 69 |
| poxB_downstream_For | tactagcgcagcttaagctcgcaatagtgactacattcgc | 70 |
| poxB_downstream_Rev | cagcagcctaggttacgtgatgacctgcggccc | 71 |
| nfrA_upstream_For | actgaaccgctctagtgtgcggccaggcgtcgtagtgc | 72 |
| nfrA_upstream_Rev | tagctgtaaatctaggggcttccggacgatccg | 73 |
| nfrA_downstream_For | tactagcgcagcttaggcgagcagtttttgcgc | 74 |
| nfrA_downstream_Rev | cagcagcctaggttaacagaaaaataacgacgaagcaacc | 75 |

By substituting the PAM sequence with the CAAA sequence, it is possible to prevent the foreign gene insertion site that has already been introduced and expressed in the subsequent repeated steps of transformation from being cleaved by Cas9 again.

In order to insert the 3-HP producing gene cassette recombinant vector, the sequences of the homology arms acting on the gene targeted to the guide RNA so that the guide RNA sequence of Table 2 acts on the *E. coli* genome to be inserted were shown in Table 4 below.

TABLE 4

| homology arm | homology arm sequence (5'→3') | SEQ ID NO |
|---|---|---|
| ldhA_upstream | ggcgattgggatgtgtgcattacccaacggcaaacgctgtagcgaacagtca<br>cttgccgccgggagctgtggcagctattaattcattaaatccgccagcttataa<br>gttaatgtctgttttgcggtcgccagcgttaactggttcgcggtcagatccactt<br>gtgcaccttctttcagcatttcgctaatggtgttatcgagttcattaagctgcggg<br>ttagcgcacatcatacgggtcattgccagccctttggc | 18 |
| ldhA_downstream | tactagcgcagcttaagctcaaagccaaaggactcgttcacctgttgcaggta<br>cttcttgtcgtactgttttgtgctataaacggcgagtttcataagactttctccagt<br>gatgttgaatcacatttaagctactaaaaatatttacaaaatttcaaatttaattg<br>aaagctatggcgatattgaaaaattcatcaacaactatgcttagtgtaggcgca<br>accttcaactgaacggttaaacatgccacaatac | 19 |
| yqhD_upstream | ggcggagttaatcccgctggctgccatcgacggctggaaatgctcatcttcg<br>ccaatgtccatcaacagttcctgtaactgcaaaatatcgacattgagacgcaa<br>ccctgccagcggcacctctgacgtggcataggtttcgcactcaaacggcaac<br>ggcaccgtcagcagcaggtattcattggcatcataacgaaacacgcgttcatt<br>gatataaccgattttatgcccggaaaagagaattatgatgccagg | 20 |
| yqhD_downstream | tactagcgcagcttagaacagtatgttaccaaaccggttgatgccaaaattca<br>ggaccgtttcgcagaaggcattttgctgacgctaatcgaagatggtccgaaa<br>gccctgaaagagccagaaaactacgatgtgcgcgccaacgtcatgtgggc<br>ggcgactcaggcgctgaacggtttgattggcgctggcgtaccgcaggactg<br>ggcaacgcatatgctgggccacgaactgactgcgatgcacggtctggat | 21 |
| glpK_upstream | ccgggttgttgattttcttcggtgtgggttgcgttgcagcactaaaagtcgctgg<br>tgcgtcttttggtcagtgggaaatcagtgtcatttggggactgggggtggcaat<br>ggccatctacctgaccgcaggggtttccggcgcgcatcttaatcccgctgtta<br>ccattgcattgtggctgtttgcctgtttcgacaagcgcaaagttattccttttatcg<br>tttcacaagttgccggcgctttctgtgctgcggctt | 22 |
| glpK_downstream | tactagcgcagcttaacctatggcactggctgctttatgctgatgaacactggc<br>gagaaagcggtgaaatcagaaaacggcctgctgaccaccatcgcctgcgg<br>cccgactggcgaagtgaactatgcgttggaaggtgcggtgtttatggcaggc<br>gcatccattcagtggctgcgcgatgaaatgaagttgattaacgacgcctacga<br>ttccgaatatttcgccaccaaagtgcaaaacaccaatggtgtgtat | 23 |
| gldA_upstream | catgcacgaagaattccgtaacgcgctggttaacgccgcctctgccgacgct<br>atcgccagcctgctgcaacatgaactggaactgtaaaaggaaacatcatgga<br>actgtatctggacaccgctaacgtcgcagaagtcgaacgtctggcacgcata<br>ttccccattgccggggtgacaactaacccgagcattatcgctgccagcaagg<br>agtccatatgggaagtgctgccgcgtctgcaaaaagcgattggtgat | 24 |

TABLE 4-continued

| homology arm | homology arm sequence (5'→3') | SEQ ID NO |
|---|---|---|
| gldA_downstream | tactagcgcagcttagaagcggcatgtgcagaaggtgaaaccattcacaaca<br>tgcctggcggcgcgacgccagatcaggtttacgccgctctgctggtagccg<br>accagtacggtcagcgtttcctgcaagagtgggaataacctactccaaactcc<br>cggcttgtccgggagtttgaacgcaaaattgcctgatgcgctacgcttatcag<br>gcctacgcaatctctgcaatatattgaatttgcgtgcttttgtagg | 25 |
| mgsA_upstream | gattgtgattctggagaaaggtcgctttatcagcccgtggaagcatattctggtt<br>gatgaatttcaggatatctcgccgcagcgggcagcgttgttagcggcattacg<br>caagcaaaacagtcagacgacgttgttcgctgttggtgatgactggcaggcg<br>atttaccgattcagcggtgcgcaaatgtcgctcaccaccgctttccatgaaaa<br>ctttggtgaaggcgaacgctgtgatttagacacgacttaccg | 26 |
| mgsA_downstream | tactagcgcagcttatccgcgcaggtaaagtgcgagtcgtcagttccataatg<br>tacatccgtagttaactttcctacagattactgtaagcacttatcgctgcaagata<br>aagaccgaaaaagcctgcgcacaggcacaaaaatctcaggaagatggttgt<br>ttttccgcccactgcaggaaagtatttcgcgtttgtgggtcagccagtttaaacc<br>aatacttcagccgttgttctgtgagcacctgagactgcgg | 27 |
| poxB_upstream | ttaccttagccagtttgttttcgccagttcgatcacttcatcaccgcgtccgctga<br>tgattgcgcgcagcatatacaggctgaaacctttggcctgttcgagtttgatct<br>gcggtggaatggctaactcttctttggcgaccaccacatccaccaacaccgg<br>accgtcgatggagaaggcgcgttgcagggcttcatcaacttcagacgcttttt<br>ctacacggatacccgtaatgccgcacgcttcggcaatgcg | 28 |
| poxB_downstream | tactagcgcagcttaagctcgcaatagtgactacattcgcggaatagctcttgt<br>gggtgggtttcctggaaatagccgctgccaatttcgctggagggaatatgag<br>cggcaatcgccagtaccggaacgtgattgcggtggcaatcgaacaggccgt<br>tgattaagtgcaggttgccggggccgcacgatccggcgcagaccgccagtt<br>ctccgctaagttgtgcttcagcgccagcggcaaaggccgccacttct | 29 |
| nfrA_upstream | tgtgcggccaggcgtcgtagtgcgtctcgccggtccagatattccagcggac<br>cccgactccgccaagctgcgcgccctgagtgcctttatcacgatagccgttgt<br>cctgaacgtgagcgtaaggctcaatagtctgtccgttagctaccttctgatgcc<br>agctgacgcgataatctgccgtccacgcctgaatatcctggcggatatattgc<br>gccgcatcgaggtacaggttttgggcaaaccagcctgaaccgt | 30 |
| nfrA_downstream | tactagcgcagcttaggcgagcagtttttgcgctgcgtcgtactgaccttctttt<br>aacagcaccggtagcgtcgcgccaacaacatactggcggttgtcggcaaac<br>tgtaccgtataattcgccaacgcctgaacggggttagcgctgtatttagataac<br>agatagagccaacttttctcttgtgcgtccgtggtaaatagtggcttattttcaat<br>gagataatgctggaggcgtgctttttcgccacgataagc | 31 |

The homology arm connection part and the cassette recombinant vector were shown in FIG. 2 and FIG. 3, respectively.

Example 2. Gene Deletion and Preparation of Strain in Which 3-Hydroxypropionic Acid (3-HP) Producing Gene is Inserted Into Genomic DNA The common recombinant vector, G recombinant vector and D recombinant DNA prepared in Example 1 were transduced into W3110 which was a strain in which yqhD, glpK, ldhA, ack-pta and gldA genes were deleted from *E. coli* W3110 strain (purchased from KCTC) (ΔyghD, ΔglpK, ΔldhA, Δack-pta and ΔgldA) (named as DKALG strain) with 5 copy numbers, 6 copy numbers and 7 copy numbers, respectively. After that, a transformant was prepared by expressing Cas9 and RED recombinase of the common recombinant vector.

Transducing 5 copy numbers into the DKALG strain was transducing using ldhA, gldA, glpK, yqhD and mgsA (5) sgRNA of Example 1-2 above as the G recombinant vector, and transducing 6 copy numbers was transducing using ldhA, gldA, glpK, yghD, mgsA and poxB (6) sgRNA of Example 1-2 above, and transducing 7 copy numbers was transducing using ldhA, gldA, glpK, yghD, mgsA, poxB and nfrA (7) sgRNA of Example 1-2 above.

Specifically, the *E. coli* strain was cultured to be between O.D (600 nm) 0.5 to 1 under the condition of 37° C. Celsius, and was washed with DW (distilled water) twice and then each recombinant vector 50 to 100 ng was added for electroporation to select a colony. In case of the D recombinant DNA, it was introduced in a linear form or introduced as the vector as it is, by enzymatic treatment or performing PCR for the prepared vector.

Then, the selected colony was cultured in an LB medium at 37° C. Celsius, and arabinose was added at a concentration of 0.1 to 1% (w/v) to express RED recombinase, and was further cultured at 37° C. Celsius for 1 hour.

Colony PCR was performed for the prepared transformant, to select a transformed strain, and until removal of the selected transformant G recombinant vector was confirmed, by culturing at 37° C. while performing cell streaking, the G recombinant vector was removed from the transformant. Specifically, by smearing in an ampicillin-added LB-agar plate and an LB-agar plate, respectively, a strain in which growth and development were confirmed in a kanamycin-added medium, but growth was not done in an ampicillin-added medium was selected.

In case of the colony PCR, considering that the efficiency of Taq polymerase is sharply reduced when amplifying DNA of 5 kb or more, primers were designed so that about 1.0~1.5 kb regions were to be amplified to near 5' of the dhab1 gene inserted from the 100 bp upstream region of the 5' homology arm region, to confirm whether the target gene was inserted, and the specific information of the primers was shown in Table 5 below.

TABLE 5

| Primer Name | Sequence (5'→3') | SEQ ID NO |
|---|---|---|
| poxB_For | agtgtgcgcaccagatgc | 32 |
| poxB_Rev | gtttgccgtccagttcgacga | 33 |
| nfrA_For | cgctctccgttacgttgattaatcg | 34 |
| nfrA_Rev | gtttgccgtccagttcgacga | 35 |
| mgsA_For | gaaggcagaaaacgctgtcg | 36 |
| mgsA_Rev | gtttgccgtccagttcgacga | 37 |
| ldhA_For | caatgatcggcggttcgc | 38 |
| ldhA_Rev | gtttgccgtccagttcgacga | 39 |
| yqhD_For | cacgtcgagtaaccgc | 40 |
| yqhD_Rev | gtttgccgtccagttcgacga | 41 |
| gldA_For | ctgcgggcgatcagcatatg | 42 |
| gldA_Rev | gtttgccgtccagttcgacga | 43 |
| glpK_For | gctgtttgcctgtttcgacaagc | 44 |
| glpK_Rev | gtttgccgtccagttcgacga | 45 |

Comparative Example 1. Preparation of Strain in Which 3-HP Producing Gene Plasmid Vector is Inserted In order to proceed an experiment using a 3-HP producing gene plasmid vector, the pCDF_J23101_dhaB_gdrAB_J23100_aldH_btuR vector of Korean Patent Publication No. 10-2020-0051375 having 20-30 copy numbers was prepared, and the structure of the corresponding vector was shown in FIG. 4.

In addition, by purifying with qiagen PCR purification kit, after treating xbaI and bglII restriction enzymes (Thermo Scientific) to the pRSFDuet-1 (Merck Millipore 71341) vector, purified fragments of the vector were obtained. After that, for the pCDF_J23101_dhaB_gdrAB_J23100_aldH_btuR vector, PCR was performed using primers of Table 6 below, and by treating the xbaI and bglII restriction enzymes and purifying with qiagen PCR purification kit, purified fragments of the 3-HP producing gene cassette recombinant vector were obtained.

TABLE 6

| Primer name | Primer sequence (5'→3') | SEQ ID NO: |
|---|---|---|
| 3-HP_For | ctagatttacagctagctcagtcc | 46 |
| 3-HP_Rev | tgccatattaataatcgatccctatctgc | 47 |

The purified fragments of the pRSFDuet-1 vector obtained through the purification process were connected with the purified fragments of the 3-HP producing gene cassette recombinant vector with NEB T4 ligase (NEB M0202S) to prepare a 3-HP producing gene plasmid vector, and the structure of the prepared vector was shown in FIG. 5.

The prepared pCDF_J23101_dhaB_gdrAB_J23100_aldH_btuR vector and pRSFDuet-1 vector-based 3-HP producing gene plasmid vector was transformed by introducing it into the DKALG strain of Example 2 by electroporation using an electroporation device (Eppendorf Eporator), thereby preparing a strain in which the 3-HP producing gene plasmid based on the pRSFDuet-1 vector was inserted (3-HP_pRSF) and a strain in which the pCDF_J23101_dhaB_gdrAB_J23100_aldH_btuR vector plasmid was inserted (3-HP_pCDF).

Example 3. Cell 2-Step Culture and 3-HP Production

Culture was carried out through a 2-step culture method using a minimal medium (M9_Gly) containing only glycerol as a carbon source for the strains in which the 3-HP producing gene prepared in Example 2 was inserted into genomic DNA with 5 copy numbers (3-HP_5gD), 6 copy numbers (3-HP_6gD) and 7 copy numbers (3-HP_7gD), respectively, and the strain in which the 3-HP producing gene plasmid vector prepared in Comparative example 1 was inserted with 20-30 copy numbers (3-HP_pCDF) and the strain in which the 3-HP producing gene plasmid vector was inserted with 100 copy numbers or more (3-HP_pRSF).

The strains were inoculated with 1% in LB medium (growth medium) 50 mL and grown at 37° C. for 24 hours (first step culture), and whole cells were collected by centrifugation and the supernatant was discarded. Thereafter, the collected whole cells were added to a minimal medium containing purified water, M9 minimal medium salt, glycerol, magnesium sulfate and calcium chloride (M9_Gly; production medium) and cultured under the condition of 200 rpm at 37° C. for 24 hours or more (second step culture) to collect samples every predetermined time, and then confirm the 3-HP production by HPLC.

The LB medium is a medium prepared by dissolving BD Difco Miller Luria-Bertani product in DW (distilled water) at a concentration of 25 g/L and then autoclave sterilizing at 121° C. for 15 minutes, and the minimal medium (M9_Gly) is a medium containing Disodium phosphate 6 g, Monopotassium phosphate 3 g, Ammonium chloride 1 g, Sodium chloride 0.5 g, 1M $CaCl_2$ 0.1 ml, 1M $MgSO_4$ 2 ml, 5 mM Vitamin $B_{12}$ 0.1 ml and Glycerol 20 g per 1 L of medium. The HPLC measurement condition was shown in Table 7 below.

TABLE 7

| | |
|---|---|
| Detector | RI / UV detector |
| Column | Bio-Rad Aminex HPX-87H Ion Exclusion Column 300 mm × 7.8 mm |
| Mobile phase | 0.5 mM H2SO4 |
| Flow rate | 0.4 mL/min |
| Run time | 35 min |
| Column temperature | 35° C. |
| Detector temperature | 35° C. |
| Injection volume | 5 μL |

Comparative Example 2. Strain Culture and 3-HP Production in the Conventional Way Additionally, for comparison with the conventional way, using the strain in which the 3-HP producing gene plasmid vector prepared in Comparative example 1 was inserted with 20-30 copy numbers (3-HP_pCDF) and the strain in which the 3-HP producing gene plasmid vector was inserted with 100 copy numbers or more (3-HP_pRSF), they were cultured in a minimal medium containing Disodium phosphate 6 g, Monopotassium phosphate 3 g, Ammonium chloride 1 g, Sodium chloride 0.5 g, 1M $CaCl_2$) 0.1 ml, 1M $MgSO_4$ 2 ml, 5 mM Vitamin B12 0.1 ml, Glycerol 20 g, Glucose 5 g and 5% Streptomycin 0.1 ml per 1 L of medium (M9_Glu).

Specifically, the strains (3-HP_pCDF and 3-HP_pRSF) were inoculated in the LB medium of Example 3 and cultured under the condition of 37° C., 200 RPM for 24 hours, and then the saturated culturing solution was inoculated in the minimal medium (M9_Glu) by 1 (v/v) % volume, and then, in the same manner, culturing which proceeds growth and production simultaneously was carried out under the condition of 37° C., 200 RPM for 24 hours.

Example 4. 3-HP Production Measurement Result According to Culture Method

The cell concentration measured through absorbance measurement measured in Example 3 and Comparative example 2 above and the 3-HP concentration measured in Example 3 and Comparative example 2 above were shown in Table 8 below.

TABLE 8

| Type of used strain | Used production medium | Cell concentration ($OD_{600}$) | 3-HP concentration (g/L) | 3-HP concentration / cell concentration ($OD_{600}$) |
|---|---|---|---|---|
| 3-HP_5gD | M9_Gly | 3.84 | 4.06 | 1.057 |
| 3-HP_6gD | M9_Gly | 3.78 | 4.9 | 1.296 |
| 3-HP_7gD | M9_Gly | 3.63 | 5.3 | 1.460 |
| 3-HP_pCDF | M9_Glu | 0.429 | 0.1967 | 0.459 |
| 3-HP_pRSF | M9_Glu | 0.477 | 0.1311 | 0.275 |
| 3-HP_pCDF | M9_Gly | 2.395 | 4.8790 | 2.037 |
| 3-HP_pRSF | M9_Gly | 2.978 | 0.8319 | 0.279 |

As a result, in case of the strain in which the 3-HP producing gene was inserted into genomic DNA, a linear 3-HP concentration increase was confirmed as the gene copy number increased, and through this, it was confirmed that the corresponding strain was appropriate for confirmation of recombinant gene performance.

However, in case of the strain in which the plasmid vector was inserted, when comparing the 3-HP concentration produced by the 3-HP_pRSF strain with 100 copy numbers or more and 3-HP_pCDF with 20-30 copy numbers, it was not possible to confirm a 3-HP concentration increase according to the increase in the copy number, and through this, it was confirmed that the corresponding strain was not suitable for confirming recombinant gene performance.

Through this, it was confirmed that the target gene should be inserted into genomic DNA, not inserted in a plasmid vector form, in order to confirm recombinant gene performance.

Example 5. Confirmation of Change in 3-HP Production According to Increase in Transduced Copy Number In order to confirm the change in the 3-HP production of the strain transduced with a higher copy number (10, 12 copy numbers) than the strain in which the 3-HP producing gene transduction confirmed in Example 4 above was done with 5 and 7 copy numbers, the 3-HP production was confirmed in a 5 L fermenter (Working volume 2 L).

5-1. Recombinant Vector and Recombinant DNA Preparation

By the substantially same method as Example 1-2 above, the G recombinant vector was prepared, and the G recombinant vector was prepared, using gRNA having nucleic acid sequences of Table 9 below (fhuA, fadL, adhE, pflB and aldA) additionally.

TABLE 9

| Target | gRNA sequence (5'→3') | Accession Number | SEQ ID NO | Name of the sequence |
|---|---|---|---|---|
| fhuA | TACGGCTGGTTGCCGAAAGAGGG | P06971 | 76 | fhuA_gRNA1 |
| | GCCAAAGATCCGGCAAACTCCGG | (UniProt) | 77 | fhuA_gRNA2 |
| fadL | GCACCGATTAACGACCAATTTGG | P0A8V6 (Uniprot) | 78 | fadL_gRNA1 |
| | CCTGAAATGTGGGAAGTGTCAGG | | 79 | fadL_gRNA2 |
| adhE | CGGGTGCGGGGAGAAGATAATG G | P0A9Q7 (Uniprot) | 80 | adhE_gRNA |

TABLE 9-continued

| Target | gRNA sequence (5'→3') | Accession Number | SEQ ID NO | Name of the sequence |
|---|---|---|---|---|
| pflB | CATTACTTTGTCCCACAGGGTGG | P09373 (Uniprot) | 81 | pflB_gRNA |
| aldA | GATTCACGCGTCATTAATAGTGG | P25553 (Uniprot) | 82 | aldA_gRNA |

In addition, D recombinant DNA was prepared by the substantially same method as Example 1-3 above, and primers of Table 10 below were additionally used, and homology arms having sequences of Table 11 below were further used, to prepare D recombinant DNA.

TABLE 10

| homology arm primer | homology arm sequence (5'→3') | SEQ ID NO |
|---|---|---|
| fhuA_upstream_For | ACTGAACCGCTCTAGTACCAACAATAACG TAGATACCTGG | 83 |
| fhuA_upstream_Rev | TAGCTGTAAATCTAGAGACTGTCGCGCCG CAATA | 84 |
| fhuA_downstream_For | TACTAGCGCAGCTTAGCACCGTCTAAAGG TAAGCAGT | 85 |
| fhuA_downstream_Rev | CAGCAGCCTAGGTTATCCGACGGCGGCTG ATGA | 86 |
| fadL_upstream_For | ACTGAACCGCTCTAGAAAACCTGACCCAT AACACTC | 87 |
| fadL_upstream_Rev | TAGCTGTAAATCTAGGACCATAACCTCAA TGATTTATTTT | 88 |
| fadL_downstream_For | TACTAGCGCAGCTTACGATTCACTATAGC CTGGC | 89 |
| fadL_downstream_Rev | CAGCAGCCTAGGTTAATTAACTTCATCAT TGTTATTTTCA | 90 |
| adhE_upstream_For | ACTGAACCGCTCTAGAAAGCGCAGCGCC AGCTC | 91 |
| adhE_upstream_Rev | TAGCTGTAAATCTAGACAACGGCGTAATC TGTGCTTC | 92 |
| adhE_downstream_For | TACTAGCGCAGCTTACTTGCTCTTGAGTG AAACTGGCA | 93 |
| adhE_downstream_Rev | CAGCAGCCTAGGTTATAACGCGTACCCCA GACGATG | 94 |
| pflB_upstream_For | ACTGAACCGCTCTAGCAGTGATGTACTGT TTAGCCAGCCA | 95 |
| pflB_upstream_Rev | TAGCTGTAAATCTAGGTAAATCTGGTGTT CTGACCGGTCT | 96 |
| pflB_downstream_For | TACTAGCGCAGCTTAGTAACACCTACCTT CTTAAGTGGA | 97 |
| pflB_downstream_Rev | CAGCAGCCTAGGTTAGGCGAGATATGATC TATATCAATTT | 98 |
| aldA_upstream_For | ACTGAACCGCTCTAGATGCACCACGCTGG TTAAGT | 99 |
| aldA_upstream_Rev | TAGCTGTAAATCTAGTATTACCGGTCAAA AGAGCGGG | 100 |
| aldA_downstream_For | TACTAGCGCAGCTTAAAACCTTTGGCCCG GTGC | 101 |
| aldA_downstream_Rev | CAGCAGCCTAGGTTAGGTGCGAAGAAGG TGTTGATTTCC | 102 |

TABLE 11

| homology arm | homology arm sequence (5'→3') | SEQ ID NO |
|---|---|---|
| fhuA_upstream | taccaacaataacgtagatacctggtttgcgggcattgacggcagcacggtg<br>accatcacctgggtcggccgtgataacaaccagccgaccaaactgtatggtg<br>ccagcggggcaatgtcgatttatcagcgttatctggctaaccagacgccaac<br>gccgctgaatcttgttccgccagaagatattgcagatatgggcgtggactacg<br>acggcaactttgtttgcagcggtggcatgcgtatcttgccggtctggaccagc<br>gatccgcaatcgctgtgccagcagagcgagatgcagcagcagccgtcagg<br>caatccgtttgatcagtcttctcagccgcagcaacagccgcaacagcaacct<br>gctcagcaagagcagaaagacagcgacggtgtagccggttggatcaagga<br>tatgtttggtagtaattaacatctaagcgtgaaataccggatggcgagttgcca<br>tccggtaaaataacatcccatctaagatattaaccctttcttttcatctggttgttta<br>ttaacccttcaggaacgctcagattgcgtaccgcttgcgaacccgccagcgtt<br>tcgaatattatcttatctttataataatcattctcgtttacgttatcattcactttacat<br>cagagatataccaatggcgcgttccaaaactgctcagccaaaacactcactg<br>cgtaaaatcgcagttgtagtagccacagcggttagcggcatgtctgtttatgca<br>caggcagcggttgaaccgaaagaagacactatcaccgttaccgctgcacct<br>gcgccgcaagaaagcgcatgggggcctgctgcaactattgcggcgcgaca<br>gtct | 103 |
| fhuA_downstream | gcaccgtctaaaggtaagcagtatgaagtcggcgtgaaatatgtaccggaag<br>atcgtccgattgtagttactggtgccgtgtataatctcactaaaaccaacaacct<br>gatggcggaccctgagggttccttcttctcggttgaaggtggcgagatccgc<br>gcacgtggcgtagaaatcgaagcgaaagcggcgctgtcggcgagtgttaa<br>cgtagtcggttcttatacttacaccgatgcggaatacaccaccgatactaccta<br>taaaggcaatacgcctgcacaggtgccaaaacacatggcttcgttgtgggct<br>gactacaccttctttgacggtccgctttcaggtctgacgctgggcaccggtgg<br>tcgttatactggctccagttatggtgatccggctaactcctttaaagtgggaagt<br>tatacggtcgtggatgcgttagtacgttatgatctggcgcgagtcggcatggc<br>tggctccaacgtggcgctgcatgttaacaacctgttcgatcgtgaatacgtcg<br>ccagctgctttaacacttatggctgcttctggggcgcagaacgtcaggtcgtt<br>gcaaccgcaaccttccgtttctaatttctcttttggggcacggatttccgtgccc<br>atttcacaagttggctgttatgcaggaatacacgaatcattccgataccactttt<br>gcactgcgtaatatctcctttcgtgtgcccgggcgcacgcttttgcatccgctg<br>tcgttaacctttcctgccgggaaagtgaccggtctgattggtcacaacggttct<br>ggtaaatccactctgctcaaaatgcttggccgtcatcagccgccgtcgga | 104 |
| fadL_upstream | aaaacctgacccataacactcccctgtaaaaaaataaataaagtggtctgacc<br>tgatcatagtcttaaccatttttttacatttagccaagtggagaaaagggaaagt<br>gggagctatgacacagagagaaaagaagaagagaaaagaaaacgcccct<br>gccagcaactgacaggggcgtacgtacccgagaggaattaacgcagaccc<br>agctggaaaatcagcatttcagcttcgcaggcaaaagtgaaatcgatatcca<br>ggcgcacaccgtcagactcttcagtgaaagtcggggtgattttgcaaggttca<br>gattccacgctacgggctttttcagtcagegccgccagcgtttgctctgcttct<br>gcgcggtttgcaaacacgcggctgtaagacgcggtgcagtcggagttgtcc<br>ataatggtgccaacatccatacagcagcaaaccggggtttcatcagcactac<br>atttactcatcgttgatttcctctgtatgtgcacccaaggtgccagataaacgttg<br>tggatattttacgcttccggaaagtgctgctccagttgttaattctgcaaaatcg<br>gataagtgaccgaaatcacacttaaaaatgatctaaaacaaaattcacccgaa<br>tccatgagtgcgccacctccaaattttgccagctggatcgcgtttcttagatcat<br>atttgaaaaaagatagaaacatacttgcaacattccagctggtccgacctatac<br>tctcgccactggtctgatttctaagatgtacctcagaccctacacttegcgctcc<br>tgttacagcacgtaacatagtttgtataaaaataaatcattgaggttatggtc | 105 |
| fadL_downstream | cgattcactatagcctggcttacaccagctggagtcagttccagcagctgaaa<br>gcgacctcaaccagtggcgacacgctgttccagaaacatgaaggctttaaag<br>atgcttaccgcatcgcgttgggtaccacttattactacgatgataactggacctt<br>ccgtaccggtatcgcctttgatgacagcccagttcctgcacagaatcgttctat<br>ctccattccggaccaggaccgtttctggctgagtgcaggtacgacttacgcat<br>ttaataaagatgcttcagtcgacgttggtgtttcttatatgcacggtcagagcgt<br>gaaaattaacgaaggcccataccagttcgagtctgaaggtaaagcctggctg<br>ttcggtactaactttaactacgcgttctgataacgcgttcgcctggataaagtca<br>cctgcatagcaggtgactttaactcccccacttcaccgaaagtagtgtcctcat<br>tgcttacctcctgagttttgcaaacagcctgttggcagcttgccctttcaaatca<br>ataagcggtatccacagacaaacctgaagggaaaggcatattttcaggcgtt<br>ctgctcgtccttctcaaagagtttacttttctgcatttccaggatactccccccc<br>ctggctattgtgcgctcatacactcaaattaaagataggttctaaataaatgagc<br>gtttttgatagtctatttcattaggtaatatatatttgtaacaaatcaatcaaaatg<br>gaataaaatcatgctaccatctatttcaatcaacaataccagcgcagcttaccc<br>agaatccatcaatgaaaataacaatgatgaagttaat | 106 |
| adhE_upstream | aaagcgcagcgccagctcttcgaagtgagtttccggatgttcgtacataaccc<br>acatgatcttcgcggcgtccatcggggaaccaccacccagcgcgataatca<br>cgtctggtttgaaggagtttgccagttctgcacctttacgaacgatgctcaggg<br>tcgggtccgcttctacttcgaagaagacttcagtttcaacgcctgctgctttcag<br>tacggaagtgatctgatcagcataaccattgttgaacaggaagcggtcagtca<br>cgatgagcgcacgtttgtggccatcagtaatcacttcatccagcgcgattggc<br>agggagccacggcggaagtagatagatttcggaagtttgtgccacaacatgt<br>tttcagctcgcttagcaacggttttcttgttgatcaggtgtttcggaccaacgtttt<br>cagagatggagttaccaccccaagaaccacaacccagagtcagggaaggt | 107 |

TABLE 11-continued

| homology arm | homology arm sequence (5'→3') | SEQ ID NO |
|---|---|---|
| | gcgagtttgaagttatacaggtcaccgataccaccctgagacgctggggtgtt<br>aatcaggatacgcgccgttttcattttctgaccgaagtaagaaacgcgagccg<br>gttggttatcctggtcagtgtacaggcaagaggtatgaccgataccgcccata<br>gcaaccagtttctctgctttttctaccgcgtcttcgaaatctttagcgcggtacat<br>tgccagagtcggggacagttttcatgtgcgaacggttcgctttcatcaacaac<br>ggtcacttcaccgatcagaatcttggtgttttctggtacagagaagcctgccag<br>ttcagcaattttataggctggctgaccaacgatagccgcgttcagcgcaccgt<br>ttttcaggataacatcctgaacagctttcagctctttaccctgcaacagatagcc<br>gccgtgggttgcaaaacgttcacgtacagcgtcataaacagagtcaacaaca<br>acaacagactgttcagaagcacagattacgccgttgt | |
| adhE_downstream | cttgctcttgagtgaaactggcatattcacgctgggctttttttacacgctctacg<br>agtgcgttaagttcagcgacattagtaacagccataatgctctcctgataatgtt<br>aaactttttttagtaaatcatctgctcgaatacgagagtatagtcagtgcggtgat<br>gatttgcttaacctatgaaaatcaaaagcttactcgcgctcacactcactgtgat<br>ttactaaaagagtttaaacattagagttattatctctaatgcgtcacttccaggtg<br>gcgtaagcaagattactcacttctgggtactgattacgtgatccaaatcaaattt<br>ttgcaaagctgacacctttcagcatcgcttttcgccattatagctaacagttaata<br>aattgtagtatgatttggtggctacattagcatgttttgcacaactagataacaat<br>aacgaatgatagcaattttaagtagttaggaggtgaaaaatgctgtcaaaagg<br>cgtattgtcagcgcgtcttttcaaccttatttatggctaacattatccggcttttgct<br>tcggagctaaccgtgattcagacctttttgattttcccgtttacttcaaatttttcat<br>cgggttatttgcgctggtcaacccggtagggattattcccgtctttatcagcatg<br>accagttatcagacagcggcagcgcgaaacaaaactaaccttacagccaac<br>ctgtctgtggccattatcttgtggatctcgcttttttctcggcgacacgattctaca<br>actttttggtatatcaattgattcgttccgtatcgccgggggtatcctggtggtga<br>caatagcgatgtcgatgatcagcggcaagcttggcgaggataaacagaaca<br>agcaagaaaaatcagaaaccgcggtacgtgaaagcattggtgtggtgccac<br>tggcgttgccgttgatggggggccaggggcgatcagttctaccatcgtctg<br>gggtacgcgtta | 108 |
| pflB_upstream | cagtgatgtactgtttagccagccagtccatgaagtgatccatgcgctccatca<br>cttcatcatagttcaggacatcgcctttgatcggttcagacttcggaccaacct<br>gcattttcagtttttcgtcaacgccgccgttgattgcgtacagcatggttttcgcc<br>aggtttgcacgcgcaccgaagaactgcatttgtttaccaacgatcatcgggct<br>tacgcagcaagcaatagcgtagtcatcgttgttgaagtccggacgcatcagg<br>tcatcgttctcatactgcagagaagaggtgtcgatggacactttagcggcgaa<br>tttcttgaagttcagcggcagtttttcagaccacagaatggtcatgttcggttcc<br>ggagacggacccatggtgtacagggtgttcaggaaacggaagctgtttttgg<br>taaccagggtacgaccgtcgaggcccataccaccgatagattcggttgccca<br>gatcgggtcgccagagaacagttcatcgtattccggagtacgcaggaagcg<br>aaccatacgcagtttcatgaccaggtggtcaaccatttcctgcgcttcttgttcg<br>gtgatcttgccagctttcaggtcacgttcgatgtacacatccaggaaggtgga<br>ggtacgaccgaaggacattgcagcaccgttctgagacttaacagcagccag<br>gtagccgaagtaagtccactggatagcttcctgagcgttggtagccggacca<br>gagatgtcgtagccgtatttcgcagccatttctttcatctgacccagagcgcgg<br>tgctgttcagcgatttcttcgcgcagacggatagtctgttccaggtttacgccgt<br>tttccagatcagcctgcagagaagtgaactgtgccagtttgtctttcatcaggta<br>gtcgataccgtacagcgcaacgcgacggtagtcaccgatgatacggccacg<br>gccatatgcatctggcagaccggtcagaacaccagatttac | 109 |
| pflB_downstream | gtaacacctaccttcttaagtggatttttatttactgcgtacttcgacaaccatta<br>atggtggtcgttttcacgcaggtaaatgacccagtatgtcaacccaaccaaca<br>aaccaccaccgataatgttgccgatcgtaaccggaatcaggttatcagtgatg<br>aaattcatcacggtcaggtgagaaaaattttccggtgcagaaccgactgcggt<br>ccaaaattccggggatgcgaagtcgcggattacaatacccatcgggatcata<br>aacatgtttgcgatactgtgctcaaaaccgctggcaacaaacatcgcgaccg<br>gcagcaccataatgaacgctttgtccatcaggctgcggccagaataactcatc<br>catactgccagacataccatcaggtttgccaggataccaagacagacggcct<br>caataaaagtatggtgcactttgtggtcggcggtttgtaggacgtttagtcccc<br>attgaccatttgcggtcatatactcgccggaaagccacattaaaagtacaaac<br>agcagtgcgccgaccaggttgccaaaatagacatttagccagtttttcgccaa<br>ctgaccccaggtgatgcgcccactcgccttagcaacaacaatcaacacggt<br>ggaagtaaagagatcggctccgcagacaacacaaagaatcagccccagag<br>agaagcaaatgccgccaaccagttttgccatgccgaagggcattgtgcctgt<br>gccagtggttgctgtgatatagaagacgaatgcgattgagatgaaaacaccg<br>gcggtaatcgccagatagaaagtcttaagcggatgtttcgttgctttatagaca<br>cccgcctcttcggccactttggccattgcagcaggaagtaaaagatcaaaag<br>ggttgtcagctttcacactaactctctctttattaagtcggcgacgagatactaa<br>caaagcattatagatgagaaattgatatagatcatatctcgcc | 110 |
| aldA_upstream | atgcaccacgctggttaagttatcccggattcgttcctcagttaggaaataacg<br>cagacagtgtaatctttattaatcagttacaaggattatggccagttgagcgtta<br>tctctcactactcactggcgagctgccgcgtttacgcgatgatagcgatggct<br>acggtccccgcgggcgagattttatcgttcacgttgattttccggcagaagtca<br>tccatgcatggcaaacgctgaaacatgatgcggtgctcatcgaggcgatgga<br>aagtcgctcgttacgttaaaaattgcccgtttgtgaaccacttgtttgcaaacgg<br>gcatgactcctgactttttatttctgccttttattccttttacacttgtttttatgaagcc | 111 |

TABLE 11-continued

| homology arm | homology arm sequence (5'→3') | SEQ ID NO |
|---|---|---|
| | cttcacagaattgtcctttcacgattccgtctctctgatgattgatgttaattaaca atgtattcaccgaaaacaaacatataaatcacaggagtcgcccatgtcagtac ccgttcaacatcctatgtatatcgatggacagtttgttacctggcgtggagacg catggattgatgtggtaaaccctgctacagaggctgtcatttcccgcataccc gatggtcaggccgaggatgcccgtaaggcaatcgatgcagcagaacgtgc acaaccagaatgggaagcgttgcctgctattgaacgcgccagttggttgcgc aaaatctccgccgggatccgcgaacgcgccagtgaaatcagtgcgctgatt gttgaagaaggggcaagatccagcagctggctgaagtcgaagtggctttta ctgccgactatatcgattacatggcggagtgggcacggcgttacgagggcg agattattcaaagcgatcgtccaggagaaaatattcttttgtttaaacgtgcgctt ggtgtgactaccggcattctgccgtggaacttcccgttcttcctcattgcccgc aaaatggctcccgctcttttgaccggtaata | |
| aldA_downstream | aaacctttggcccggtgctgccagttgtcgcatttgacacgctggaagatgct atctcaatggctaatgacagtgattacggcctgacctcatcaatctatacccaa aatctgaacgtcgcgatgaaagccattaaagggctgaagtttggtgaaactta catcaaccgtgaaaacttcgaagctatgcaaggcttccacgccggatggcgt aaatccggtattggcggcgcagatggtaaacatggcttgcatgaatatctgca gacccaggtggtttatttacagtcttaatgagtgaaagaggcggaggtttttcc tccgcctgtgcgcgtcagagtttagcgaatttttcgagggtgcgaataagctgt gtgacgaagccatattcgttatcgtaccaggcgaccgttttcaccagttgtaaa tcgcccacggcggtaatttccgtttgcgtggcatcaaacaccgaaccgaaat ggctgccaatgatatcggaagagactatttcttcatcggtataaccaaatgact cgttattggtggttgcttgtttaagtgcgttattcacctcttcggcagtcactttttt ccgagaatcgataccagttcagtgaccgaacctgttttcaccggcacgcgttg cgcatgacctttcagtttgccgctcagttccgggatcaccagaccaatggcttt tgccgcccccgtagtgtggggaatgatatttctgccgctgcgcgtgaagcac gtaaatctttaccacgcgggccatccaccagtgactgggtgccagtataggc atgaatggtcgtcatcgtgccgacttctatcccgaaactgtcatgcaaggcttt ggccatcggcgcaagacagttagtggtgcatgacgccacggaaacaatggt gtcgttgccatccagagtgtcgtcattgacgttataaacgatagttttcatttcac cggcaggggcggaaatcaacaccttcttcgcacc | 112 |

5-2. Gene Deletion and Preparation of Strain in Which 3-HP Producing Gene is Inserted Into Genomic DNA The common recombinant vector prepared in Example 1-1, G recombinant vector and D recombinant DNA prepared in Example 5-1 were transduced into W3110 which was a strain in which yqhD, glpK, ldhA, ack-pta and gldA genes were deleted from *E. coli* W3110 strain (purchased from KCTC) (ΔyqhD, ΔglpK, ΔldhA, Δack-pta and ΔgldA) (named as DKALG strain) with 5 copy numbers, 7 copy numbers, 10 copy numbers and 12 copy numbers, respectively. After that, a transformant was prepared by expressing Cas9 and RED recombinase of the common recombinant vector.

The 5-copy number and 7-copy number transducing was performed by the substantially same method as Example 2 above, and the 10-copy number transducing was transducing using ldhA, gldA, glpK, yghD, mgsA, poxB, nfrA, fhuA, fadL and adhE (10) sgRNA of Example 5-1 above, and the 12-copy number transducing was transducing using ldhA, gldA, glpK, yghD, mgsA, poxB, nfrA, fhuA, fadL, adhE, pflB and aldA (12) sgRNA. In addition, in order to confirm insertion of the target gene, using primers of Table 12 below in addition to the primers used in Example 2 above, insertion of the target gene was confirmed.

TABLE 12

| Primer Name | Primer Sequence (5'→3') | SEQ ID NO |
|---|---|---|
| fhuA_For | tggaccatgcagcaggtggtacaac | 113 |
| fhuA_Rev | gtttgccgtccagttcgacga | 114 |
| fadL_For | gtacgtaaaccgctaacaatggcga | 115 |
| fadL_Rev | gtttgccgtccagttcgacga | 116 |
| adhE_For | ttcgggaacttgtagatacgtttac | 117 |
| adhE_Rev | gtttgccgtccagttcgacga | 118 |
| pflB_For | gtacttgtcgtgcatgtagtgga | 119 |
| pflB_Rev | gtttgccgtccagttcgacga | 120 |
| aldA_For | gttccgccgtatgactgg | 121 |
| aldA_Rev | gtttgccgtccagttcgacga | 122 |

5.3 Cell 2-Step Culture and 3-HP Production

For the strains in which the 3-HP producing gene prepared in Example 5.2 was inserted into genomic DNA with 5 copy numbers (3-HP_5gD), 7 copy numbers (3-HP_7gD), 10 copy numbers (3-HP_10gD) or 12 copy numbers (3-HP_12gD), respectively, high concentration cell culture was performed in a 5 L fermenter (Working volume 2 L) by a fed-batch culture method.

Specifically, glucose 20 g/L, and an antibiotic for selection (streptomycin) 25 mg/L was added to MR medium ($KH_2PO_4$ 6.67 g, $(NH_4)_2HPO_4$ 4 g, $MgSO_4$·7H2O 0.8 g, citric acid 0.8 g, and trace metal solution 5 mL per 1 L; herein, Trace metal solution was 5M HCl 5 mL, $FeSO_4 \cdot 7H_2O$ 10 g, $CaCl_2$ 2 g, $ZnSO_4 \cdot 7H_2O$ 2.2 g, $MnSO_4 \cdot 4H_2O$ 0.5 g, $CuSO_4 \cdot 5H_2O$ 1 g, $(NH_4)_6Mo_7O_2 \cdot 4H_2O$ 0.1 g, and $Na_2B_4O_2 \cdot 10H_2O$ 0.02 g per 1 L) and it was used as a cell culture medium, and the temperature of 35° C. Celsius was maintained. pH was maintained at 6.95 using ammonia water, and the dissolved oxygen amount (DO) was maintained at 20% while increasing the stirring speed step-wise up to 900 rpm, and the aeration was maintained at 1 vvm, and the fed-batch culture was performed using the pH-stat feeding method, and glucose was added at 3 g/L.

After completing the high concentration cell culture of 20 hours, the cell culture solution was centrifuged at 6,000 rpm at 4 degrees Celsius for 10 minutes to recover cells. The recovered cells were suspended in PBS (phosphate-buffered saline) and used in the next step.

The medium for 3-HP production was prepared by adding 70 g/L of glycerol and 50 uM of vitamin $B_{12}$ to M9 medium comprising no glucose. The cell suspension prepared above was inoculated into the medium for 3-HP production so that the cell inoculum amount was 5 g/L (based on dry cell weight), and the 3-HP production step was performed in a 5 L fermenter (Working volume 2 L). The culture condition for 3-HP production was that the temperature was maintained at 35° C. Celsius, and the stirring speed was maintained at 300 rpm, and the aeration was maintained at 1 vvm, and the pH was maintained at 7.0 using $Ca(OH)_2$, and it was proceeded for 24 hours.

The 3-HP concentration over time in the 3-HP production process was measured by high pressure liquid chromatography (High Pressure; HPLC), and the result was shown in Table 13 below.

TABLE 13

| Type of used strain | 3-HP concentration (g/L) |
|---|---|
| 3-HP_5gD | 64.6 |
| 3-HP_7gD | 75.6 |
| 3-HP_10gD | 91.0 |
| 3-HP_12gD | 115.5 |

As a result, as confirmed in Example 4 above, in case of the strain in which the 3-HP producing gene was inserted into genomic DNA, a linear 3-HP concentration increase was confirmed as the gene copy number increased, and in particular, in case of inserting the gene of 10 copy numbers and 12 copy numbers, a linear 3-HP concentration increase was confirmed. Through this, it was confirmed that the corresponding strain was suitable for confirmation of recombinant gene performance, and inserting a target gene into genomic DNA for confirmation of recombinant gene performance was appropriate.

The invention claimed is:

1. An *Escherichia coli* bacterium having 3-hydroxypropionic acid (3-HP) producing ability, wherein:

(i) at least one gene selected from the group consisting of yghD, glpK, IdhA, ack-pta, and gldA is deleted; and (ii) a foreign 3-HP producing gene is inserted into genomic DNA in one or more copies at insertion target sites of ldhA, gldA, glpK, yqhD, and mgsA.

2. The *Escherichia coli* bacterium having 3-HP producing ability according to claim 1, wherein the foreign 3HP producing gene comprises genes encoding glycerol dehydratase, aldehyde dehydrogenase, glycerol dehydratase reactivase and adenosyltransferase.

3. The *Escherichia coli* bacterium having 3-HP producing ability according to claim 1, wherein the *Escherichia coli* bacterium comprises deletion of yqhD, glpK, ldhA, ack-pta and gldA.

4. The *Escherichia coli* bacterium having 3-HP producing ability according to claim 1, wherein the foreign 3-HP producing gene is further inserted into genomic DNA at one or more insertion target sites selected from the group consisting of IdhA, gldA, glpK, yqhD, mgsA, poxB, nfrA, fhuA, fadL, adhE, pflB and aldA.

5. The *Escherichia coli* bacterium having 3-HP producing ability according to claim 1, wherein the foreign 3-HP producing gene is inserted into genomic DNA by CRISPR-Cas9 system.

6. The *Escherichia coli* bacterium having 3-HP producing ability according to claim 1, wherein 3-HP production increases in proportion to the copy number of the inserted foreign 3-HP producing gene.

7. The *Escherichia coli* bacterium having 3-HP producing ability according to claim 1, wherein 3-HP production increases in proportionally with the copy number within a range of 5 to 12 copies.

8. A method for producing 3-hydroxypropionic acid (3-HP), comprising:

culturing an *Escherichia coli* bacterium comprising a foreign 3-HP producing gene inserted into genomic DNA thereof, wherein:

(i) the *Escherichia coli* bacterium comprises deletion of at least one gene selected from the group consisting of yqhD, glpK, IdhA, ack-pta, and gldA; and (ii) the foreign 3-HP producing gene is inserted into genomic DNA in one or more copies at insertion target sites of ldhA, gldA, glpK, yqhD, and mgsA.

9. The method of claim 8, wherein the foreign 3-HP producing gene comprises genes encoding glycerol dehydratase, aldehyde dehydrogenase, glycerol dehydratase reactivase, and adenosyltransferase.

10. The method of claim 8, wherein the *Escherichia coli* bacterium comprises deletion of yqhD, glpK, IdhA, ack-pta, and gldA.

11. The method of claim 8, wherein the foreign 3-HP producing gene is further inserted into genomic DNA at one or more insertion target sites selected from the group consisting of poxB, nfrA, fhuA, fadL, adhE, pflB, and aldA.

12. The method of claim 8, wherein the insertion of the foreign 3-HP producing gene is performed using a CRISPR-Cas9 system.

13. The method of claim 8, wherein culturing the *Escherichia coli* bacterium comprises:

a first culturing step in a medium comprising glucose as a carbon source; and a second culturing step in a medium not comprising glucose as a carbon source.

14. The method of claim 8, wherein 3-HP production increases in proportion to the copy number of the inserted foreign 3-HP producing gene.

15. The method of claim 8, wherein 3-HP production increases proportionally with the copy number within a range of 5 to 12 copies.

* * * * *

SEQUENCE LISTING

```
Sequence total quantity: 122
SEQ ID NO: 1           moltype = DNA  length = 4107
FEATURE                Location/Qualifiers
misc_feature           1..4107
                       note = Cas9 gene
source                 1..4107
                       mol_type = other DNA
                       organism = synthetic construct
SEQUENCE: 1
atggataaga aatactcaat aggcttagat atcggcacaa atagcgtcgg atgggcggtg  60
atcactgatg aatataaggt tccgtctaaa aagttcaagg ttctgggaaa tacagaccgc  120
cacagtatca aaaaaaatct tataggggct cttttatttg acagtggaga gacagcggaa  180
gcgactcgtc tcaaacggac agctcgtaga aggtatacac gtcggaagaa tcgtatttgt  240
tatctacagg agatttttc aaatgagatg gcgaaagtag atgatagttt ctttcatcga  300
cttgaagagt ctttttggt ggaagaagac aagaagcatg aacgtcatcc tattttgga  360
aatatagtag atgaagttgc ttatcatgag aaatatccaa ctatctatca tctgcgaaaa  420
aaattggtag attctactga taaagcggat ttgcgcttaa tctatttggc cttagcgcat  480
atgattaagt ttcgtggtca tttttgatt gagggagatt taaatcctga taatagtgat  540
gtggacaaac tatttatcca gttggtacaa acctacaatc aattatttga agaaaaccct  600
attaacgcaa gtggagtaga tgctaaagcg attctttctg cacgattgag taaatcaaga  660
cgattagaaa atctcattgc tcagctcccc ggtgagaaga aaaatggctt atttgggaat  720
ctcattgctt tgtcattggg tttgacccct aattttaaat caaattttga tttggcagaa  780
gatgctaaat tacagctttc aaaagatact tacgatgatg atttagataa tttattggcg  840
caaattggag atcaatatgc tgatttgttt ttggcagcta agaatttatc agatgctatt  900
ttactttcag atatcctaag agtaaatact gaaataacta aggctcccct atcagcttca  960
atgattaaac gctacgatga acatcatcaa gacttgactc ttttaaaagc tttagttcga  1020
caacaacttc cagaaaagta taaagaaatc tttttgatc aatcaaaaaa cggatatgca  1080
ggttatattg atgggggagc tagccaagaa gaattttata aatttatcaa accaatttta  1140
gaaaaaatgg atggtactga ggaattattg gtgaaactaa atcgtgaaga tttgctgcgc  1200
aagcaacgga cctttgacaa cggctctatt ccccatcaaa ttcacttggg tgagctgcat  1260
gctatttga gaagacaaga agacttttat ccatttttaa aagacaatcg tgagaagatt  1320
gaaaaaatct tgacttttcg aattccttat tatgttggtc cattggcgcg tggcaatagt  1380
cgttttgcat ggatgactcg gaagtctgaa gaaacaatta ccccatggaa ttttgaagaa  1440
gttgtcgata aaggtgcttc agctcaatca tttattgaac gcatgacaaa ctttgataaa  1500
aatcttccaa atgaaaagt actaccaaaa catagtttgc tttatgagta ttttacggtt  1560
tataacgaat tgacaaaggt caaatatgtt actgaaggaa tgcgaaaacc agcatttctt  1620
tcaggtgaac agaagaaagc cattgttgat ttactcttca aaacaaatcg aaaagtaacc  1680
gttaagcaat taaaagaaga ttatttcaaa aaaatagaat gttttgatag tgttgaaatt  1740
tcaggagttg aagatagatt taatgcttca ttaggtacct accatgattt gctaaaaatt  1800
attaaagata aagatttttt ggataatgaa gaaaatgaag atatcttaga ggatattgtt  1860
ttaacattga ccttatttga agatagggag atgattgagg aaagacttaa aacatatgct  1920
cacctctttg atgataaggt gatgaaacag cttaaacgtc gccgttatac tggttgggga  1980
cgtttgtctc gaaaattgat taatggtatt agggataagc aatctggcaa aacaatatta  2040
gatttttga aatcagatgg ttttgccaat cgcaatttta tgcagctgat ccatgatgat  2100
agtttgacat ttaaagaaga cattcaaaaa gcacaagtgt ctggacaagg cgatagttta  2160
catgaacata ttgcaaattt agctggtagc cctgctatta aaaaaggtat tttacagact  2220
```

-continued

```
gtaaaagttg ttgatgaatt ggtcaaagta atggggcggc ataagccaga aaatatcgtt  2280
attgaaatgg cacgtgaaaa tcagacaact caaaagggcc agaaaaattc gcgagagcgt  2340
atgaaacgaa tcgaagaagg tatcaaagaa ttaggaagtc agattcttaa agagcatcct  2400
gttgaaaata ctcaattgca aaatgaaaag ctctatctct attatctcca aaatggaaga  2460
gacatgtatg tggaccaaga attagatatt aatcgtttaa gtgattatga tgtcgatcac  2520
attgttccac aaagtttcct taaagacgat tcaatagaca ataaggtctt aacgcgttct  2580
gataaaaatc gtggtaaatc ggataacgtt ccaagtgaag aagtagtcaa aaagatgaaa  2640
aactattgga gacaacttct aaacgccaag ttaatcactc aacgtaagtt tgataattta  2700
acgaaagctg aacgtggagg tttgagtgaa cttgataaag ctggttttat caaacgccaa  2760
ttggttgaaa ctcgccaaat cactaagcat gtggcacaaa ttttggatag tcgcatgaat  2820
actaaatacg atgaaaatga taaacttatt cgagaggtta aagtgattac cttaaaatct  2880
aaattagttt ctgacttccg aaaagatttc caattctata aagtacgtga gattaacaat  2940
taccatcatg cccatgatgc gtatctaaat gccgtcgttg gaactgcttt gattaagaaa  3000
tatccaaaac ttgaatcgga gtttgtctat ggtgattata aagtttatga tgttcgtaaa  3060
atgattgcta agtctgagca agaaataggc aaagcaaccg caaaatattt cttttactct  3120
aatatcatga acttcttcaa aacagaaatt acacttgcaa atggagagat tcgcaaacgc  3180
cctctaatcg aaactaatgg ggaaactgga gaaattgtct gggataaagg gcgagatttt  3240
gccacagtgc gcaaagtatt gtccatgccc caagtcaata ttgtcaagaa aacagaagta  3300
cagacaggcg gattctccaa ggagtcaatt ttaccaaaaa gaaattcgga caagcttatt  3360
gctcgtaaaa aagactggga tccaaaaaaa tatggtggtt ttgatagtcc aacggtagct  3420
tattcagtcc tagtggttgc taaggtggaa aaagggaaat cgaagaagtt aaaatccgtt  3480
aaagagttac tagggatcac aattatggaa agaagttcct ttgaaaaaaa tccgattgac  3540
tttttagaag ctaaaggata taaggaagtt aaaaaagact taatcattaa actacctaaa  3600
tatagtcttt ttgagttaga aaacggtcgt aaacggatgc tggctagtgc cggagaatta  3660
caaaaaggaa atgagctggc tctgccaagc aaatatgtga atttttttata tttagctagt  3720
cattatgaaa agttgaaggg tagtccagaa gataacgaac aaaaacaatt gtttgtggag  3780
cagcataagc attatttaga tgagattatt gagcaaatca gtgaattttc taagcgtgtt  3840
attttagcag atgccaattt agataaagtt cttagtgcat ataacaaaca tagagacaaa  3900
ccaatacgtg aacaagcaga aaatattatt catttattta cgttgacgaa tcttggagct  3960
cccgctgctt ttaaatattt tgatacaaca attgatcgta aacgatatac gtctacaaaa  4020
gaagttttag atgccactct tatccatcaa tccatcactg gtctttatga aacacgcatt  4080
gatttgagtc agctaggagg tgactga                                      4107

SEQ ID NO: 2            moltype = DNA  length = 1885
FEATURE                 Location/Qualifiers
misc_feature            1..1885
                        note = RED recomgbinase gene
source                  1..1885
                        mol_type = other DNA
                        organism = synthetic construct
SEQUENCE: 2
atggatatta atactgaaac tgagatcaag caaaagcatt cactaacccc ctttcctgtt  60
ttcctaatca gcccggcatt tcgcgggcga tattttcaca gctatttcag gagttcagcc  120
atgaacgctt attacattca ggatcgtctt gaggctcaga gctgggcgcg tcactaccag  180
cagctcgccc gtgaagagaa agaggcagaa ctggcagacg acatggaaaa aggcctgccc  240
cagcacctgt ttgaatcgct atgcatcgat catttgcaac gccacggggc cagcaaaaaa  300
tccattaccc gtgcgtttga tgacgatgtt gagtttcagg agcgcatggc agaacacatc  360
cggtacatgg ttgaaaccat tgctcaccac caggttgata ttgattcaga ggtataaaac  420
gaatgagtac tgcactcgca acgctggctg ggaagctggc tgaacgtgtc ggcatggatt  480
ctgtcgaccc acaggaactg atcaccactc ttcgccagac ggcatttaaa ggtgatgcca  540
gcgatgcgca gttcatcgca ttactgatcg ttgccaacca gtacggcctt aatccgtgga  600
cgaaagaaat ttacgccttt cctgataagc agaatggcat cgttccggtg gtgggcgttg  660
atggctggtc ccgcatcatc aatgaaaacc agcagtttga tggcatggac tttgagcagg  720
acaatgaatc ctgtacatgc cggatttacc gcaaggaccg taatcatccg atctgcgtta  780
ccgaatggat ggatgaatgc cgccgcgaac cattcaaaac tcgcgaaggc agagaaatca  840
cggggccgtg gcagtcgcat cccaaacgga tgttacgtca taaagccatg attcagtgtg  900
cccgtctggc cttcggattt gctggtatct atgacaagga tgaagccgag cgcattgtcg  960
aaaatactgc atacactgca gaacgtcagc cggaacgcga catcactccg gttaacgatg  1020
aaaccatgca ggagattaac actctgctga tcgccctgga taaaacatgg gatgacgact  1080
tattgccgct ctgttcccag atatttcgcc gcgacattcg tgcatcgtca gaactgacac  1140
aggccgaagc agtaaaagct cttggattcc tgaaacagaa agccgcagag cagaaggtgg  1200
cagcatgaca ccggacatta tcctgcagcg taccgggatc gatgtgagag ctgtcgaaca  1260
gggggatgat gcgtggcaca aattacggct cggcgtcatc accgcttcag aagttcacaa  1320
cgtgatagca aaaccccgct ccggaaagaa gtggcctgac atgaaaatgt cctacttcca  1380
caccctgctt gctgaggttt gcaccggtgt ggctccggaa gttaacgcta aagcactggc  1440
ctggggaaaa cagtacgaga acgacgccag aaccctgttt gaattcactt ccggcgtgaa  1500
tgttactgaa tccccgatca tctatcgcga cgaaagtatg cgtaccgcct gctctcccga  1560
tggtttatgc agtgacggca acggccttga actgaaatgc ccgtttacct cccgggattt  1620
catgaagttc cggctcggtg gtttcgaggc cataaagtca gcttacatgg cccaggtgca  1680
gtacagcatg tgggtgacgc gaaaaaatgc ctggtacttt gccaactatg acccgcgtat  1740
gaagcgtgaa ggcctgcatt atgtcgtgat tgagcgggat gaaaagtaca tggcgagttt  1800
tgacgagatc gtgccggagt tcatcgaaaa aatggacgag gcactggctg aaattggttt  1860
tgtatttggg gagcaatggc gatga                                        1885

SEQ ID NO: 3            moltype = DNA  length = 20
FEATURE                 Location/Qualifiers
misc_feature            1..20
                        note = ldhA_gRNA1
```

```
source                  1..20
                        mol_type = other DNA
                        organism = synthetic construct
SEQUENCE: 3
gcacgttgtg gcaggcagac                                              20

SEQ ID NO: 4            moltype = DNA  length = 20
FEATURE                 Location/Qualifiers
misc_feature            1..20
                        note = ldhA_gRNA2
source                  1..20
                        mol_type = other DNA
                        organism = synthetic construct
SEQUENCE: 4
taacgtctga ttcagagaac                                              20

SEQ ID NO: 5            moltype = DNA  length = 20
FEATURE                 Location/Qualifiers
misc_feature            1..20
                        note = ldhA_gRNA3
source                  1..20
                        mol_type = other DNA
                        organism = synthetic construct
SEQUENCE: 5
aacgtctgat tcagagaaca                                              20

SEQ ID NO: 6            moltype = DNA  length = 20
FEATURE                 Location/Qualifiers
misc_feature            1..20
                        note = yqhD_gRNA1
source                  1..20
                        mol_type = other DNA
                        organism = synthetic construct
SEQUENCE: 6
actttcctgc tggcggttgg                                              20

SEQ ID NO: 7            moltype = DNA  length = 20
FEATURE                 Location/Qualifiers
misc_feature            1..20
                        note = yqhD_gRNA2
source                  1..20
                        mol_type = other DNA
                        organism = synthetic construct
SEQUENCE: 7
caccaaattt atcgccgcag                                              20

SEQ ID NO: 8            moltype = DNA  length = 20
FEATURE                 Location/Qualifiers
misc_feature            1..20
                        note = glpK_gRNA1
source                  1..20
                        mol_type = other DNA
                        organism = synthetic construct
SEQUENCE: 8
attgtctggg aaaaagaaac                                              20

SEQ ID NO: 9            moltype = DNA  length = 20
FEATURE                 Location/Qualifiers
misc_feature            1..20
                        note = glpK_gRNA2
source                  1..20
                        mol_type = other DNA
                        organism = synthetic construct
SEQUENCE: 9
cgtcgttctt ccgaagtata                                              20

SEQ ID NO: 10           moltype = DNA  length = 20
FEATURE                 Location/Qualifiers
misc_feature            1..20
                        note = gldA_gRNA1
source                  1..20
                        mol_type = other DNA
                        organism = synthetic construct
SEQUENCE: 10
atcgcggaga ctgcgcagtg                                              20

SEQ ID NO: 11           moltype = DNA  length = 20
FEATURE                 Location/Qualifiers
```

```
misc_feature          1..20
                      note = gldA_gRNA2
source                1..20
                      mol_type = other DNA
                      organism = synthetic construct
SEQUENCE: 11
cctcgatact gccaaagcac                                        20

SEQ ID NO: 12         moltype = DNA  length = 20
FEATURE               Location/Qualifiers
misc_feature          1..20
                      note = mgsA_gRNA1
source                1..20
                      mol_type = other DNA
                      organism = synthetic construct
SEQUENCE: 12
cgagataacg ctgataatcg                                        20

SEQ ID NO: 13         moltype = DNA  length = 20
FEATURE               Location/Qualifiers
misc_feature          1..20
                      note = mgsA_gRNA2
source                1..20
                      mol_type = other DNA
                      organism = synthetic construct
SEQUENCE: 13
cgcagcaagg ctttcacgtc                                        20

SEQ ID NO: 14         moltype = DNA  length = 20
FEATURE               Location/Qualifiers
misc_feature          1..20
                      note = poxB_gRNA1
source                1..20
                      mol_type = other DNA
                      organism = synthetic construct
SEQUENCE: 14
cagtgcatgg ttgccccttc                                        20

SEQ ID NO: 15         moltype = DNA  length = 20
FEATURE               Location/Qualifiers
misc_feature          1..20
                      note = poxB_gRNA2
source                1..20
                      mol_type = other DNA
                      organism = synthetic construct
SEQUENCE: 15
gtacttgtgg gatctgctcc                                        20

SEQ ID NO: 16         moltype = DNA  length = 20
FEATURE               Location/Qualifiers
misc_feature          1..20
                      note = nfrA_gRNA1
source                1..20
                      mol_type = other DNA
                      organism = synthetic construct
SEQUENCE: 16
cgcatgcagc caccagtaga                                        20

SEQ ID NO: 17         moltype = DNA  length = 20
FEATURE               Location/Qualifiers
misc_feature          1..20
                      note = nfrA_gRNA2
source                1..20
                      mol_type = other DNA
                      organism = synthetic construct
SEQUENCE: 17
ccagtcgcgc cattaaagtc                                        20

SEQ ID NO: 18         moltype = DNA  length = 255
FEATURE               Location/Qualifiers
misc_feature          1..255
                      note = ldhA_upstream
source                1..255
                      mol_type = other DNA
                      organism = synthetic construct
SEQUENCE: 18
ggcgattggg atgtgtgcat tacccaacgg caaacgctgt agcgaacagt cacttgccgc  60
cgggagctgt ggcagctatt aattcattaa atccgccagc ttataagtta atgtctgttt  120
tgcggtcgcc agcgttaact ggttcgcggt cagatccact tgtgcacctt ctttcagcat  180
```

```
ttcgctaatg gtgttatcga gttcattaag ctgcgggtta gcgcacatca tacgggtcat  240
tgccagccct ttggc                                                   255

SEQ ID NO: 19           moltype = DNA  length = 255
FEATURE                 Location/Qualifiers
misc_feature            1..255
                        note = ldhA_downstream
source                  1..255
                        mol_type = other DNA
                        organism = synthetic construct
SEQUENCE: 19
tactagcgca gcttaagctc aaagccaaag gactcgttca cctgttgcag gtacttcttg  60
tcgtactgtt ttgtgctata aacggcgagt ttcataagac tttctccagt gatgttgaat  120
cacatttaag ctactaaaaa tattttacaa aatttcaaat ttaattgaaa gctatggcga  180
tattgaaaaa ttcatcaaca actatgctta gtgtaggcgc aaccttcaac tgaacggtta  240
aacatgccac aatac                                                   255

SEQ ID NO: 20           moltype = DNA  length = 255
FEATURE                 Location/Qualifiers
misc_feature            1..255
                        note = yqhD_upstream
source                  1..255
                        mol_type = other DNA
                        organism = synthetic construct
SEQUENCE: 20
ggcggagtta atcccgctgg ctgccatcga cggctggaaa tgctcatctt cgccaatgtc  60
catcaacagt tcctgtaact gcaaaatatc gacattgaga cgcaaccctg ccagcggcac  120
ctctgacgtg gcataggttt cgcactcaaa cggcaacggc accgtcagca gcaggtattc  180
attggcatca taacgaaaca cgcgttcatt gatataaccg attttatgcc cggaaaagag  240
aattatgatg ccagg                                                   255

SEQ ID NO: 21           moltype = DNA  length = 255
FEATURE                 Location/Qualifiers
misc_feature            1..255
                        note = yqhD_downstream
source                  1..255
                        mol_type = other DNA
                        organism = synthetic construct
SEQUENCE: 21
tactagcgca gcttagaaca gtatgttacc aaaccggttg atgccaaaat tcaggaccgt  60
ttcgcagaag gcattttgct gacgctaatc gaagatggtc cgaaagccct gaaagagcca  120
gaaaactacg atgtgcgcgc caacgtcatg tgggcggcga ctcaggcgct gaacggtttg  180
attggcgctg gcgtaccgca ggactgggca acgcatatgc tgggccacga actgactgcg  240
atgcacggtc tggat                                                   255

SEQ ID NO: 22           moltype = DNA  length = 255
FEATURE                 Location/Qualifiers
misc_feature            1..255
                        note = glpK_upstream
source                  1..255
                        mol_type = other DNA
                        organism = synthetic construct
SEQUENCE: 22
ccgggttgtt gattttcttc ggtgtgggtt gcgttgcagc actaaaagtc gctggtgcgt  60
cttttggtca gtgggaaatc agtgtcattt ggggactggg ggtggcaatg gccatctacc  120
tgaccgcagg ggtttccggc gcgcatctta atcccgctgt taccattgca ttgtggctgt  180
ttgcctgttt cgacaagcgc aaagttattc cttttatcgt ttcacaagtt gccggcgctt  240
tctgtgctgc ggctt                                                   255

SEQ ID NO: 23           moltype = DNA  length = 255
FEATURE                 Location/Qualifiers
misc_feature            1..255
                        note = glpK_downstream
source                  1..255
                        mol_type = other DNA
                        organism = synthetic construct
SEQUENCE: 23
tactagcgca gcttaaccta tggcactggc tgctttatgc tgatgaacac tggcgagaaa  60
gcggtgaaat cagaaaacgg cctgctgacc accatcgcct gcggcccgac tggcgaagtg  120
aactatgcgt tggaaggtgc ggtgtttatg gcaggcgcat ccattcagtg gctgcgcgat  180
gaaatgaagt tgattaacga cgcctacgat tccgaatatt tcgccaccaa agtgcaaaac  240
accaatggtg tgtat                                                   255

SEQ ID NO: 24           moltype = DNA  length = 255
FEATURE                 Location/Qualifiers
misc_feature            1..255
                        note = gldA_upstream
```

```
source                  1..255
                        mol_type = other DNA
                        organism = synthetic construct
SEQUENCE: 24
catgcacgaa gaattccgta acgcgctggt taacgccgcc tctgccgacg ctatcgccag  60
cctgctgcaa catgaactgg aactgtaaaa ggaaacatca tggaactgta tctggacacc  120
gctaacgtcg cagaagtcga acgtctggca cgcatattcc ccattgccgg ggtgacaact  180
aacccgagca ttatcgctgc cagcaaggag tccatatggg aagtgctgcc gcgtctgcaa  240
aaagcgattg gtgat                                                   255

SEQ ID NO: 25           moltype = DNA  length = 255
FEATURE                 Location/Qualifiers
misc_feature            1..255
                        note = gldA_downstream
source                  1..255
                        mol_type = other DNA
                        organism = synthetic construct
SEQUENCE: 25
tactagcgca gcttagaagc ggcatgtgca gaaggtgaaa ccattcacaa catgcctggc  60
ggcgcgacgc cagatcaggt ttacgccgct ctgctggtag ccgaccagta cggtcagcgt  120
ttcctgcaag agtgggaata acctactcca aactcccggc ttgtccggga gtttgaacgc  180
aaaattgcct gatgcgctac gcttatcagg cctacgcaat ctctgcaata tattgaattt  240
gcgtgctttt gtagg                                                   255

SEQ ID NO: 26           moltype = DNA  length = 255
FEATURE                 Location/Qualifiers
misc_feature            1..255
                        note = mgsA_upstream
source                  1..255
                        mol_type = other DNA
                        organism = synthetic construct
SEQUENCE: 26
gattgtgatt ctggagaaag gtcgctttat cagcccgtgg aagcatattc tggttgatga  60
atttcaggat atctcgccgc agcgggcagc gttgttagcg gcattacgca agcaaaacag  120
tcagacgacg ttgttcgctg ttggtgatga ctggcaggcg atttaccgat tcagcggtgc  180
gcaaatgtcg ctcaccaccg ctttccatga aaactttggt gaaggcgaac gctgtgattt  240
agacacgact taccg                                                   255

SEQ ID NO: 27           moltype = DNA  length = 255
FEATURE                 Location/Qualifiers
misc_feature            1..255
                        note = mgsA_downstream
source                  1..255
                        mol_type = other DNA
                        organism = synthetic construct
SEQUENCE: 27
tactagcgca gcttatccgc gcaggtaaag tgcgagtcgt cagttccata atgtacatcc  60
gtagttaact ttcctacaga ttactgtaag cacttatcgc tgcaagataa agaccgaaaa  120
agcctgcgca caggcacaaa aatctcagga agatggttgt ttttccgccc actgcaggaa  180
agtatttcgc gtttgtgggt cagccagttt aaaccaatac ttcagccgtt gttctgtgag  240
cacctgagac tgcgg                                                   255

SEQ ID NO: 28           moltype = DNA  length = 255
FEATURE                 Location/Qualifiers
misc_feature            1..255
                        note = poxB_upstream
source                  1..255
                        mol_type = other DNA
                        organism = synthetic construct
SEQUENCE: 28
ttaccttagc cagtttgttt tcgccagttc gatcacttca tcaccgcgtc cgctgatgat  60
tgcgcgcagc atatacaggc tgaaaccttt ggcctgttcg agtttgatct gcggtggaat  120
ggctaactct tctttggcga ccaccacatc caccaacacc ggaccgtcga tggagaaggc  180
gcgttgcagg gcttcatcaa cttcagacgc tttttctaca cggatacccg taatgccgca  240
cgcttcggca atgcg                                                   255

SEQ ID NO: 29           moltype = DNA  length = 255
FEATURE                 Location/Qualifiers
misc_feature            1..255
                        note = poxB_downstream
source                  1..255
                        mol_type = other DNA
                        organism = synthetic construct
SEQUENCE: 29
tactagcgca gcttaagctc gcaatagtga ctacattcgc ggaatagctc ttgtgggtgg  60
gtttcctgga aatagccgct gccaatttcg ctggagggaa tatgagcggc aatcgccagt  120
accggaacgt gattgcggtg gcaatcgaac aggccgttga ttaagtgcag gttgccgggg  180
ccgcacgatc cggcgcagac cgccagttct ccgctaagtt gtgcttcagc gccagcggca  240
aaggccgcca cttct                                                   255
```

```
SEQ ID NO: 30           moltype = DNA  length = 255
FEATURE                 Location/Qualifiers
misc_feature            1..255
                        note = nfrA_upstream
source                  1..255
                        mol_type = other DNA
                        organism = synthetic construct
SEQUENCE: 30
tgtgcggcca ggcgtcgtag tgcgtctcgc cggtccagat attccagcgg accccgactc  60
cgccaagctg cgcgccctga gtgcctttat cacgatagcc gttgtcctga acgtgagcgt  120
aaggctcaat agtctgtccg ttagctacct tctgatgcca gctgacgcga taatctgccg  180
tccacgcctg aatatcctgg cggatatatt gcgccgcatc gaggtacagg ttttgggcaa  240
accagcctga accgt                                                   255

SEQ ID NO: 31           moltype = DNA  length = 255
FEATURE                 Location/Qualifiers
misc_feature            1..255
                        note = nfrA_downstream
source                  1..255
                        mol_type = other DNA
                        organism = synthetic construct
SEQUENCE: 31
tactagcgca gcttaggcga gcagtttttg cgctgcgtcg tactgacctt cttttaacag  60
caccggtagc gtcgcgccaa caacatactg gcggttgtcg gcaaactgta ccgtataatt  120
cgccaacgcc tgaacggggt tagcgctgta tttagataac agatagagcc aacttttctc  180
ttgtgcgtcc gtggtaaata gtggcttatt ttcaatgaga taatgctgga ggcgtgcttt  240
ttcgccacga taagc                                                   255

SEQ ID NO: 32           moltype = DNA  length = 18
FEATURE                 Location/Qualifiers
misc_feature            1..18
                        note = poxB_For
source                  1..18
                        mol_type = other DNA
                        organism = synthetic construct
SEQUENCE: 32
agtgtgcgca ccagatgc                                               18

SEQ ID NO: 33           moltype = DNA  length = 21
FEATURE                 Location/Qualifiers
misc_feature            1..21
                        note = poxB_Rev
source                  1..21
                        mol_type = other DNA
                        organism = synthetic construct
SEQUENCE: 33
gtttgccgtc cagttcgacg a                                           21

SEQ ID NO: 34           moltype = DNA  length = 25
FEATURE                 Location/Qualifiers
misc_feature            1..25
                        note = nfrA_For
source                  1..25
                        mol_type = other DNA
                        organism = synthetic construct
SEQUENCE: 34
cgctctccgt tacgttgatt aatcg                                       25

SEQ ID NO: 35           moltype = DNA  length = 21
FEATURE                 Location/Qualifiers
misc_feature            1..21
                        note = nfrA_Rev
source                  1..21
                        mol_type = other DNA
                        organism = synthetic construct
SEQUENCE: 35
gtttgccgtc cagttcgacg a                                           21

SEQ ID NO: 36           moltype = DNA  length = 20
FEATURE                 Location/Qualifiers
misc_feature            1..20
                        note = mgsA_For
source                  1..20
                        mol_type = other DNA
                        organism = synthetic construct
SEQUENCE: 36
gaaggcagaa aacgctgtcg                                             20
```

-continued

```
SEQ ID NO: 37          moltype = DNA  length = 21
FEATURE                Location/Qualifiers
misc_feature           1..21
                       note = mgsA_Rev
source                 1..21
                       mol_type = other DNA
                       organism = synthetic construct
SEQUENCE: 37
gtttgccgtc cagttcgacg a                                            21

SEQ ID NO: 38          moltype = DNA  length = 18
FEATURE                Location/Qualifiers
misc_feature           1..18
                       note = ldhA_For
source                 1..18
                       mol_type = other DNA
                       organism = synthetic construct
SEQUENCE: 38
caatgatcgg cggttcgc                                                18

SEQ ID NO: 39          moltype = DNA  length = 21
FEATURE                Location/Qualifiers
misc_feature           1..21
                       note = ldhA_Rev
source                 1..21
                       mol_type = other DNA
                       organism = synthetic construct
SEQUENCE: 39
gtttgccgtc cagttcgacg a                                            21

SEQ ID NO: 40          moltype = DNA  length = 16
FEATURE                Location/Qualifiers
misc_feature           1..16
                       note = yqhD_For
source                 1..16
                       mol_type = other DNA
                       organism = synthetic construct
SEQUENCE: 40
cacgtcgagt aaccgc                                                  16

SEQ ID NO: 41          moltype = DNA  length = 21
FEATURE                Location/Qualifiers
misc_feature           1..21
                       note = yqhD_Rev
source                 1..21
                       mol_type = other DNA
                       organism = synthetic construct
SEQUENCE: 41
gtttgccgtc cagttcgacg a                                            21

SEQ ID NO: 42          moltype = DNA  length = 20
FEATURE                Location/Qualifiers
misc_feature           1..20
                       note = gldA_For
source                 1..20
                       mol_type = other DNA
                       organism = synthetic construct
SEQUENCE: 42
ctgcgggcga tcagcatatg                                              20

SEQ ID NO: 43          moltype = DNA  length = 21
FEATURE                Location/Qualifiers
misc_feature           1..21
                       note = gldA_Rev
source                 1..21
                       mol_type = other DNA
                       organism = synthetic construct
SEQUENCE: 43
gtttgccgtc cagttcgacg a                                            21

SEQ ID NO: 44          moltype = DNA  length = 23
FEATURE                Location/Qualifiers
misc_feature           1..23
                       note = glpK_For
source                 1..23
                       mol_type = other DNA
                       organism = synthetic construct
SEQUENCE: 44
gctgtttgcc tgtttcgaca agc                                          23
```

```
SEQ ID NO: 45          moltype = DNA  length = 21
FEATURE                Location/Qualifiers
misc_feature           1..21
                       note = glpK_Rev
source                 1..21
                       mol_type = other DNA
                       organism = synthetic construct
SEQUENCE: 45
gtttgccgtc cagttcgacg a                                    21

SEQ ID NO: 46          moltype = DNA  length = 24
FEATURE                Location/Qualifiers
misc_feature           1..24
                       note = 3-HP_For
source                 1..24
                       mol_type = other DNA
                       organism = synthetic construct
SEQUENCE: 46
ctagatttac agctagctca gtcc                                 24

SEQ ID NO: 47          moltype = DNA  length = 29
FEATURE                Location/Qualifiers
misc_feature           1..29
                       note = 3-HP_Rev
source                 1..29
                       mol_type = other DNA
                       organism = synthetic construct
SEQUENCE: 47
tgccatatta ataatcgatc cctatctgc                            29

SEQ ID NO: 48          moltype = DNA  length = 38
FEATURE                Location/Qualifiers
misc_feature           1..38
                       note = ldhA_upstream_For
source                 1..38
                       mol_type = other DNA
                       organism = synthetic construct
SEQUENCE: 48
actgaaccgc tctaggcgat tgggatgtgt gcattacc                  38

SEQ ID NO: 49          moltype = DNA  length = 34
FEATURE                Location/Qualifiers
misc_feature           1..34
                       note = ldhA_upstream_Rev
source                 1..34
                       mol_type = other DNA
                       organism = synthetic construct
SEQUENCE: 49
tagctgtaaa tctagatctc tctgcactgc ccgc                      34

SEQ ID NO: 50          moltype = DNA  length = 36
FEATURE                Location/Qualifiers
misc_feature           1..36
                       note = ldhA_downstream_For
source                 1..36
                       mol_type = other DNA
                       organism = synthetic construct
SEQUENCE: 50
tactagcgca gcttaagctc aaagccaaag gactcg                    36

SEQ ID NO: 51          moltype = DNA  length = 39
FEATURE                Location/Qualifiers
misc_feature           1..39
                       note = ldhA_downstream_Rev
source                 1..39
                       mol_type = other DNA
                       organism = synthetic construct
SEQUENCE: 51
cagcagccta ggttaacgat caattgcccg ctattttcc                 39

SEQ ID NO: 52          moltype = DNA  length = 34
FEATURE                Location/Qualifiers
misc_feature           1..34
                       note = yqhD_upstream_For
source                 1..34
                       mol_type = other DNA
                       organism = synthetic construct
```

```
SEQUENCE: 52
actgaaccgc tctagggcgg agttaatccc gctg                           34

SEQ ID NO: 53           moltype = DNA  length = 40
FEATURE                 Location/Qualifiers
misc_feature            1..40
                        note = yqhD_upstream_Rev
source                  1..40
                        mol_type = other DNA
                        organism = synthetic construct
SEQUENCE: 53
tagctgtaaa tctagcactt tctgttcgcg aaccagtttc                     40

SEQ ID NO: 54           moltype = DNA  length = 40
FEATURE                 Location/Qualifiers
misc_feature            1..40
                        note = yqhD_downstream_For
source                  1..40
                        mol_type = other DNA
                        organism = synthetic construct
SEQUENCE: 54
tactagcgca gcttagaaca gtatgttacc aaaccggttg                     40

SEQ ID NO: 55           moltype = DNA  length = 33
FEATURE                 Location/Qualifiers
misc_feature            1..33
                        note = yqhD_downstream_Rev
source                  1..33
                        mol_type = other DNA
                        organism = synthetic construct
SEQUENCE: 55
cagcagccta ggttaagggc tttgccgaca cct                            33

SEQ ID NO: 56           moltype = DNA  length = 34
FEATURE                 Location/Qualifiers
misc_feature            1..34
                        note = glpK_upstream_For
source                  1..34
                        mol_type = other DNA
                        organism = synthetic construct
SEQUENCE: 56
tactagcgca gcttaaccta tggcactggc tgct                           34

SEQ ID NO: 57           moltype = DNA  length = 40
FEATURE                 Location/Qualifiers
misc_feature            1..40
                        note = glpK_upstream_Rev
source                  1..40
                        mol_type = other DNA
                        organism = synthetic construct
SEQUENCE: 57
tagctgtaaa tctaggtcat attacagcga agctttttgt                     40

SEQ ID NO: 58           moltype = DNA  length = 35
FEATURE                 Location/Qualifiers
misc_feature            1..35
                        note = glpK_downstream_For
source                  1..35
                        mol_type = other DNA
                        organism = synthetic construct
SEQUENCE: 58
tactagcgca gcttaaagcg tttatgccgc atccg                          35

SEQ ID NO: 59           moltype = DNA  length = 36
FEATURE                 Location/Qualifiers
misc_feature            1..36
                        note = glpK_downstream_Rev
source                  1..36
                        mol_type = other DNA
                        organism = synthetic construct
SEQUENCE: 59
cagcagccta ggttatcttc gttgtcgcct ttgacg                         36

SEQ ID NO: 60           moltype = DNA  length = 37
FEATURE                 Location/Qualifiers
misc_feature            1..37
                        note = gldA_upstream_For
```

```
source                1..37
                      mol_type = other DNA
                      organism = synthetic construct
SEQUENCE: 60
actgaaccgc tctagcatgc acgaagaatt ccgtaac                    37

SEQ ID NO: 61         moltype = DNA  length = 39
FEATURE               Location/Qualifiers
misc_feature          1..39
                      note = gldA_upstream_Rev
source                1..39
                      mol_type = other DNA
                      organism = synthetic construct
SEQUENCE: 61
tagctgtaaa tctagaaacc taaaacaaat ttgtcaccc                  39

SEQ ID NO: 62         moltype = DNA  length = 35
FEATURE               Location/Qualifiers
misc_feature          1..35
                      note = gldA_downstream_For
source                1..35
                      mol_type = other DNA
                      organism = synthetic construct
SEQUENCE: 62
tactagcgca gcttagaagc ggcatgtgca gaagg                      35

SEQ ID NO: 63         moltype = DNA  length = 38
FEATURE               Location/Qualifiers
misc_feature          1..38
                      note = gldA_downstream_Rev
source                1..38
                      mol_type = other DNA
                      organism = synthetic construct
SEQUENCE: 63
cagcagccta ggttatctga aaccacccca atatgtgc                   38

SEQ ID NO: 64         moltype = DNA  length = 40
FEATURE               Location/Qualifiers
misc_feature          1..40
                      note = mgsA_upstream_For
source                1..40
                      mol_type = other DNA
                      organism = synthetic construct
SEQUENCE: 64
actgaaccgc tctaggattg tgattctgga gaaaggtcgc                 40

SEQ ID NO: 65         moltype = DNA  length = 38
FEATURE               Location/Qualifiers
misc_feature          1..38
                      note = mgsA_upstream_Rev
source                1..38
                      mol_type = other DNA
                      organism = synthetic construct
SEQUENCE: 65
tagctgtaaa tctagcggac cgtctgaagt aatattgc                   38

SEQ ID NO: 66         moltype = DNA  length = 33
FEATURE               Location/Qualifiers
misc_feature          1..33
                      note = mgsA_downstream_For
source                1..33
                      mol_type = other DNA
                      organism = synthetic construct
SEQUENCE: 66
tactagcgca gcttatccgc gcaggtaaag tgc                        33

SEQ ID NO: 67         moltype = DNA  length = 39
FEATURE               Location/Qualifiers
misc_feature          1..39
                      note = mgsA_downstream_Rev
source                1..39
                      mol_type = other DNA
                      organism = synthetic construct
SEQUENCE: 67
cagcagccta ggttacgaat gaatgagagc aaaagcggg                  39

SEQ ID NO: 68         moltype = DNA  length = 35
FEATURE               Location/Qualifiers
```

```
misc_feature           1..35
                       note = poxB_upstream_For
source                 1..35
                       mol_type = other DNA
                       organism = synthetic construct
SEQUENCE: 68
actgaaccgc tctagcggca ttaaagatgc gcgca                          35

SEQ ID NO: 69          moltype = DNA  length = 33
FEATURE                Location/Qualifiers
misc_feature           1..33
                       note = poxB_upstream_Rev
source                 1..33
                       mol_type = other DNA
                       organism = synthetic construct
SEQUENCE: 69
tagctgtaaa tctagacaac agcgtgctgg gct                            33

SEQ ID NO: 70          moltype = DNA  length = 40
FEATURE                Location/Qualifiers
misc_feature           1..40
                       note = poxB_downstream_For
source                 1..40
                       mol_type = other DNA
                       organism = synthetic construct
SEQUENCE: 70
tactagcgca gcttaagctc gcaatagtga ctacattcgc                     40

SEQ ID NO: 71          moltype = DNA  length = 33
FEATURE                Location/Qualifiers
misc_feature           1..33
                       note = poxB_downstream_Rev
source                 1..33
                       mol_type = other DNA
                       organism = synthetic construct
SEQUENCE: 71
cagcagccta ggttacgtga tgacctgcgg ccc                            33

SEQ ID NO: 72          moltype = DNA  length = 38
FEATURE                Location/Qualifiers
misc_feature           1..38
                       note = nfrA_upstream_For
source                 1..38
                       mol_type = other DNA
                       organism = synthetic construct
SEQUENCE: 72
actgaaccgc tctagtgtgc ggccaggcgt cgtagtgc                       38

SEQ ID NO: 73          moltype = DNA  length = 33
FEATURE                Location/Qualifiers
misc_feature           1..33
                       note = nfrA_upstream_Rev
source                 1..33
                       mol_type = other DNA
                       organism = synthetic construct
SEQUENCE: 73
tagctgtaaa tctaggggct tccggacgat ccg                            33

SEQ ID NO: 74          moltype = DNA  length = 33
FEATURE                Location/Qualifiers
misc_feature           1..33
                       note = nfrA_downstream_For
source                 1..33
                       mol_type = other DNA
                       organism = synthetic construct
SEQUENCE: 74
tactagcgca gcttaggcga gcagtttttg cgc                            33

SEQ ID NO: 75          moltype = DNA  length = 40
FEATURE                Location/Qualifiers
misc_feature           1..40
                       note = nfrA_downstream_Rev
source                 1..40
                       mol_type = other DNA
                       organism = synthetic construct
SEQUENCE: 75
cagcagccta ggttaacaga aaaataacga cgaagcaacc                     40

SEQ ID NO: 76          moltype = DNA  length = 23
```

```
FEATURE                 Location/Qualifiers
misc_feature            1..23
                        note = fhuA_gRNA1
source                  1..23
                        mol_type = other DNA
                        organism = synthetic construct
SEQUENCE: 76
tacggctggt tgccgaaaga ggg                                              23

SEQ ID NO: 77           moltype = DNA  length = 23
FEATURE                 Location/Qualifiers
misc_feature            1..23
                        note = fhuA_gRNA2
source                  1..23
                        mol_type = other DNA
                        organism = synthetic construct
SEQUENCE: 77
gccaaagatc cggcaaactc cgg                                              23

SEQ ID NO: 78           moltype = DNA  length = 23
FEATURE                 Location/Qualifiers
misc_feature            1..23
                        note = fadL_gRNA1
source                  1..23
                        mol_type = other DNA
                        organism = synthetic construct
SEQUENCE: 78
gcaccgatta acgaccaatt tgg                                              23

SEQ ID NO: 79           moltype = DNA  length = 23
FEATURE                 Location/Qualifiers
misc_feature            1..23
                        note = fadL_gRNA2
source                  1..23
                        mol_type = other DNA
                        organism = synthetic construct
SEQUENCE: 79
cctgaaatgt gggaagtgtc agg                                              23

SEQ ID NO: 80           moltype = DNA  length = 23
FEATURE                 Location/Qualifiers
misc_feature            1..23
                        note = adhE_gRNA
source                  1..23
                        mol_type = other DNA
                        organism = synthetic construct
SEQUENCE: 80
cgggtgcggg gagaagataa tgg                                              23

SEQ ID NO: 81           moltype = DNA  length = 23
FEATURE                 Location/Qualifiers
misc_feature            1..23
                        note = pflB_gRNA
source                  1..23
                        mol_type = other DNA
                        organism = synthetic construct
SEQUENCE: 81
cattactttg tcccacaggg tgg                                              23

SEQ ID NO: 82           moltype = DNA  length = 23
FEATURE                 Location/Qualifiers
misc_feature            1..23
                        note = aldA_gRNA
source                  1..23
                        mol_type = other DNA
                        organism = synthetic construct
SEQUENCE: 82
gattcacgcg tcattaatag tgg                                              23

SEQ ID NO: 83           moltype = DNA  length = 40
FEATURE                 Location/Qualifiers
misc_feature            1..40
                        note = fhuA_upstream_For
source                  1..40
                        mol_type = other DNA
                        organism = synthetic construct
SEQUENCE: 83
actgaaccgc tctagtacca acaataacgt agatacctgg                            40
```

```
SEQ ID NO: 84          moltype = DNA  length = 34
FEATURE                Location/Qualifiers
misc_feature           1..34
                       note = fhuA_upstream_Rev
source                 1..34
                       mol_type = other DNA
                       organism = synthetic construct
SEQUENCE: 84
tagctgtaaa tctagagact gtcgcgccgc aata                              34

SEQ ID NO: 85          moltype = DNA  length = 37
FEATURE                Location/Qualifiers
misc_feature           1..37
                       note = fhuA_downstream_For
source                 1..37
                       mol_type = other DNA
                       organism = synthetic construct
SEQUENCE: 85
tactagcgca gcttagcacc gtctaaaggt aagcagt                           37

SEQ ID NO: 86          moltype = DNA  length = 33
FEATURE                Location/Qualifiers
misc_feature           1..33
                       note = fhuA_downstream_Rev
source                 1..33
                       mol_type = other DNA
                       organism = synthetic construct
SEQUENCE: 86
cagcagccta ggttatccga cggcggctga tga                               33

SEQ ID NO: 87          moltype = DNA  length = 36
FEATURE                Location/Qualifiers
misc_feature           1..36
                       note = fadL_upstream_For
source                 1..36
                       mol_type = other DNA
                       organism = synthetic construct
SEQUENCE: 87
actgaaccgc tctagaaaac ctgacccata acactc                            36

SEQ ID NO: 88          moltype = DNA  length = 40
FEATURE                Location/Qualifiers
misc_feature           1..40
                       note = fadL_upstream_Rev
source                 1..40
                       mol_type = other DNA
                       organism = synthetic construct
SEQUENCE: 88
tagctgtaaa tctaggacca taacctcaat gatttatttt                        40

SEQ ID NO: 89          moltype = DNA  length = 34
FEATURE                Location/Qualifiers
misc_feature           1..34
                       note = fadL_downstream_For
source                 1..34
                       mol_type = other DNA
                       organism = synthetic construct
SEQUENCE: 89
tactagcgca gcttacgatt cactatagcc tggc                              34

SEQ ID NO: 90          moltype = DNA  length = 40
FEATURE                Location/Qualifiers
misc_feature           1..40
                       note = fadL_downstream_Rev
source                 1..40
                       mol_type = other DNA
                       organism = synthetic construct
SEQUENCE: 90
cagcagccta ggttaattaa cttcatcatt gttattttca                        40

SEQ ID NO: 91          moltype = DNA  length = 33
FEATURE                Location/Qualifiers
misc_feature           1..33
                       note = adhE_upstream_For
source                 1..33
                       mol_type = other DNA
                       organism = synthetic construct
SEQUENCE: 91
actgaaccgc tctagaaagc gcagcgccag ctc                               33
```

```
SEQ ID NO: 92          moltype = DNA  length = 37
FEATURE                Location/Qualifiers
misc_feature           1..37
                       note = adhE_upstream_Rev
source                 1..37
                       mol_type = other DNA
                       organism = synthetic construct
SEQUENCE: 92
tagctgtaaa tctagacaac ggcgtaatct gtgcttc                        37

SEQ ID NO: 93          moltype = DNA  length = 38
FEATURE                Location/Qualifiers
misc_feature           1..38
                       note = adhE_downstream_For
source                 1..38
                       mol_type = other DNA
                       organism = synthetic construct
SEQUENCE: 93
tactagcgca gcttacttgc tcttgagtga aactggca                       38

SEQ ID NO: 94          moltype = DNA  length = 36
FEATURE                Location/Qualifiers
misc_feature           1..36
                       note = adhE_downstream_Rev
source                 1..36
                       mol_type = other DNA
                       organism = synthetic construct
SEQUENCE: 94
cagcagccta ggttataacg cgtaccccag acgatg                         36

SEQ ID NO: 95          moltype = DNA  length = 40
FEATURE                Location/Qualifiers
misc_feature           1..40
                       note = pflB_upstream_For
source                 1..40
                       mol_type = other DNA
                       organism = synthetic construct
SEQUENCE: 95
actgaaccgc tctagcagtg atgtactgtt tagccagcca                     40

SEQ ID NO: 96          moltype = DNA  length = 40
FEATURE                Location/Qualifiers
misc_feature           1..40
                       note = pflB_upstream_Rev
source                 1..40
                       mol_type = other DNA
                       organism = synthetic construct
SEQUENCE: 96
tagctgtaaa tctaggtaaa tctggtgttc tgaccggtct                     40

SEQ ID NO: 97          moltype = DNA  length = 39
FEATURE                Location/Qualifiers
misc_feature           1..39
                       note = pflB_downstream_For
source                 1..39
                       mol_type = other DNA
                       organism = synthetic construct
SEQUENCE: 97
tactagcgca gcttagtaac acctaccttc ttaagtgga                      39

SEQ ID NO: 98          moltype = DNA  length = 40
FEATURE                Location/Qualifiers
misc_feature           1..40
                       note = pflB_downstream_Rev
source                 1..40
                       mol_type = other DNA
                       organism = synthetic construct
SEQUENCE: 98
cagcagccta ggttaggcga gatatgatct atatcaattt                     40

SEQ ID NO: 99          moltype = DNA  length = 35
FEATURE                Location/Qualifiers
misc_feature           1..35
                       note = aldA_upstream_For
source                 1..35
                       mol_type = other DNA
                       organism = synthetic construct
```

```
SEQUENCE: 99
actgaaccgc tctagatgca ccacgctggt taagt                         35

SEQ ID NO: 100         moltype = DNA  length = 37
FEATURE                Location/Qualifiers
misc_feature           1..37
                       note = aldA_upstream_Rev
source                 1..37
                       mol_type = other DNA
                       organism = synthetic construct
SEQUENCE: 100
tagctgtaaa tctagtatta ccggtcaaaa gagcggg                       37

SEQ ID NO: 101         moltype = DNA  length = 33
FEATURE                Location/Qualifiers
misc_feature           1..33
                       note = aldA_downstream_For
source                 1..33
                       mol_type = other DNA
                       organism = synthetic construct
SEQUENCE: 101
tactagcgca gcttaaaacc tttggcccgg tgc                           33

SEQ ID NO: 102         moltype = DNA  length = 39
FEATURE                Location/Qualifiers
misc_feature           1..39
                       note = aldA_downstream_Rev
source                 1..39
                       mol_type = other DNA
                       organism = synthetic construct
SEQUENCE: 102
cagcagccta ggttaggtgc gaagaaggtg ttgatttcc                     39

SEQ ID NO: 103         moltype = DNA  length = 850
FEATURE                Location/Qualifiers
misc_feature           1..850
                       note = fhuA_upstream
source                 1..850
                       mol_type = other DNA
                       organism = synthetic construct
SEQUENCE: 103
taccaacaat aacgtagata cctggtttgc gggcattgac ggcagcacgg tgaccatcac  60
ctgggtcggc cgtgataaca accagccgac caaactgtat ggtgccagcg gggcaatgtc  120
gatttatcag cgttatctgg ctaaccagac gccaacgccg ctgaatcttg ttccgccaga  180
agatattgca gatatgggcg tggactacga cggcaacttt gtttgcagcg gtggcatgcg  240
tatcttgccg gtctggacca gcgatccgca atcgctgtgc cagcagagcg agatgcagca  300
gcagccgtca ggcaatccgt ttgatcagtc ttctcagccg cagcaacagc cgcaacagca  360
acctgctcag caagagcaga aagacagcga cggtgtagcc ggttggatca aggatatgtt  420
tggtagtaat taacatctaa gcgtgaaata ccggatggcg agttgccatc cggtaaaata  480
acatcccatc taagatatta accctttctt ttcatctggt tgtttattaa cccttcagga  540
acgctcagat tgcgtaccgc ttgcgaaccc gccagcgttt cgaatattat cttatcttta  600
taataatcat tctcgtttac gttatcattc actttacatc agagatatac caatggcgcg  660
ttccaaaact gctcagccaa aacactcact gcgtaaaatc gcagttgtag tagccacagc  720
ggttagcggc atgtctgttt atgcacaggc agcggttgaa ccgaaagaag acactatcac  780
cgttaccgct gcacctgcgc cgcaagaaag cgcatggggg cctgctgcaa ctattgcggc  840
gcgacagtct                                                     850

SEQ ID NO: 104         moltype = DNA  length = 850
FEATURE                Location/Qualifiers
misc_feature           1..850
                       note = fhuA_downstream
source                 1..850
                       mol_type = other DNA
                       organism = synthetic construct
SEQUENCE: 104
gcaccgtcta aaggtaagca gtatgaagtc ggcgtgaaat atgtaccgga agatcgtccg  60
attgtagtta ctggtgccgt gtataatctc actaaaacca acaacctgat ggcggaccct  120
gagggttcct tcttctcggt tgaaggtggc gagatccgcg cacgtggcgt agaaatcgaa  180
gcgaaagcgg cgctgtcggc gagtgttaac gtagtcggtt cttatactta caccgatgcg  240
gaatacacca ccgatactac ctataaaggc aatacgcctg cacaggtgcc aaaacacatg  300
gcttcgttgt gggctgacta caccttcttt gacggtccgc tttcaggtct gacgctgggc  360
accggtggtc gttatactgg ctccagttat ggtgatccgg ctaactcctt taaagtggga  420
agttatacgg tcgtggatgc gttagtacgt tatgatctgg cgcgagtcgg catggctggc  480
tccaacgtgg cgctgcatgt taacaacctg ttcgatcgtg aatacgtcgc cagctgcttt  540
aacacttatg gctgcttctg gggcgcagaa cgtcaggtcg ttgcaaccgc aaccttccgt  600
ttctaatttc tcttttgggg cacggatttc cgtgcccatt tcacaagttg gctgttatgc  660
```

```
aggaatacac gaatcattcc gataccactt ttgcactgcg taatatctcc tttcgtgtgc  720
ccgggcgcac gcttttgcat ccgctgtcgt taacctttcc tgccgggaaa gtgaccggtc  780
tgattggtca caacggttct ggtaaatcca ctctgctcaa aatgcttggc cgtcatcagc  840
cgccgtcgga                                                         850

SEQ ID NO: 105         moltype = DNA  length = 850
FEATURE                Location/Qualifiers
misc_feature           1..850
                       note = fadL_upstream
source                 1..850
                       mol_type = other DNA
                       organism = synthetic construct
SEQUENCE: 105
aaaacctgac ccataacact cccctgtaaa aaaataaata aagtggtctg acctgatcat  60
agtcttaacc attttttac atttagccaa gtggagaaaa gggaaagtgg gagctatgac  120
acagagagaa aagaagaaga gaaaagaaaa cgcccctgcc agcaactgac aggggcgtac  180
gtacccgaga ggaattaacg cagacccagc tggaaaatca gcatttcagc ttcgcaggca  240
aaagtgaaat cgatatccag gcgcacaccg tcagactctt cagtgaaagt cggggtgatt  300
ttgcaaggtt cagattccac gctacgggct ttttcagtca gcgccgccag cgtttgctct  360
gcttctgcgc ggtttgcaaa cacgcggctg taagacgcgg tgcagtcgga gttgtccata  420
atggtgccaa catccataca gcagcaaacc ggggtttcat cagcactaca tttactcatc  480
gttgatttcc tctgtatgtg cacccaaggt gccagataaa cgttgtggat attttacgct  540
tccggaaagt gctgctccag ttgttaattc tgcaaaatcg gataagtgac cgaaatcaca  600
cttaaaaatg atctaaaaca aaattcaccc gaatccatga gtgcgccacc tccaaatttt  660
gccagctgga tcgcgttttct tagatcatat ttgaaaaaag atagaaacat acttgcaaca  720
ttccagctgg tccgacctat actctcgcca ctggtctgat ttctaagatg tacctcagac  780
cctacacttc gcgctcctgt tacagcacgt aacatagttt gtataaaaat aaatcattga  840
ggttatggtc                                                         850

SEQ ID NO: 106         moltype = DNA  length = 850
FEATURE                Location/Qualifiers
misc_feature           1..850
                       note = fadL_downstream
source                 1..850
                       mol_type = other DNA
                       organism = synthetic construct
SEQUENCE: 106
cgattcacta tagcctggct tacaccagct ggagtcagtt ccagcagctg aaagcgacct  60
caaccagtgg cgacacgctg ttccagaaac atgaaggctt taaagatgct taccgcatcg  120
cgttgggtac cacttattac tacgatgata actggacctt ccgtaccggt atcgcctttg  180
atgacagccc agttcctgca cagaatcgtt ctatctccat tccggaccag gaccgtttct  240
ggctgagtgc aggtacgact tacgcattta ataaagatgc ttcagtcgac gttggtgttt  300
cttatatgca cggtcagagc gtgaaaatta acgaaggccc ataccagttc gagtctgaag  360
gtaaagcctg gctgttcggt actaacttta actacgcgtt ctgataacgc gttcgcctgg  420
ataaagtcac ctgcatagca ggtgacttta actcccccac ttcaccgaaa gtagtgtcct  480
cattgcttac ctcctgagtt ttgcaaacag cctgttggca gcttgccctt tcaaatcaat  540
aagcggtatc cacagacaaa cctgaaggga aaggcatatt ttcaggcgtt ctgctcgtcc  600
ttctcaaaga gtttactttt ctgcatttcc aggatactcc cccccctgg ctattgtgcg  660
ctcatacact caaattaaag ataggttcta aataaatgag cgttttttga tagtctattt  720
cattaggtaa tatatatttg taacaaatca atcaaaatgg aataaaatca tgctaccatc  780
tatttcaatc aacaatacca gcgcagctta cccagaatcc atcaatgaaa ataacaatga  840
tgaagttaat                                                         850

SEQ ID NO: 107         moltype = DNA  length = 998
FEATURE                Location/Qualifiers
misc_feature           1..998
                       note = adhE_upstream
source                 1..998
                       mol_type = other DNA
                       organism = synthetic construct
SEQUENCE: 107
aaagcgcagc gccagctctt cgaagtgagt ttccggatgt tcgtacataa cccacatgat  60
cttcgcggcg tccatcgggg aaccaccacc cagcgcgata atcacgtctg gtttgaagga  120
gtttgccagt tctgcacctt tacgaacgat gctcagggtc gggtccgctt ctacttcgaa  180
gaagacttca gtttcaacgc ctgctgcttt cagtacggaa gtgatctgat cagcataacc  240
attgttgaac aggaagcggt cagtcacgat gagcgcacgt ttgtggccat cagtaatcac  300
ttcatccagc gcgattggca gggagccacg gcggaagtag atagatttcg gaagtttgtg  360
ccacaacatg ttttcagctc gcttagcaac ggtttttcttg ttgatcaggt gtttcggacc  420
aacgttttca gagatggagt taccacccca agaaccacaa cccagagtca gggaaggtgc  480
gagtttgaag ttatacaggt caccgatacc accctgagac gctggggtgt taatcaggat  540
acgcgccgtt ttcattttct gaccgaagta agaaacgcga gccggttggt tatcctggtc  600
agtgtacagg caagaggtat gaccgatacc gcccatagca accagtttct ctgctttttc  660
taccgcgtct tcgaaatctt tagcgcggta cattgccaga gtcggggaca gtttttcatg  720
tgcgaacggt tcgctttcat caacaacggt cacttcaccg atcagaatct tggtgttttc  780
tggtacagag aagcctgcca gttcagcaat tttataggct ggctgaccaa cgatagccgc  840
gttcagcgca ccgtttttca ggataacatc ctgaacagct ttcagctctt taccctgcaa  900
cagatagccg ccgtgggttg caaaacgttc acgtacagcg tcataaacag agtcaacaac  960
aacaacagac tgttcagaag cacagattac gccgttgt                          998
```

```
SEQ ID NO: 108          moltype = DNA  length = 998
FEATURE                 Location/Qualifiers
misc_feature            1..998
                        note = adhE_downstream
source                  1..998
                        mol_type = other DNA
                        organism = synthetic construct
SEQUENCE: 108
cttgctcttg agtgaaactg gcatattcac gctgggcttt ttttacacgc tctacgagtg  60
cgttaagttc agcgacatta gtaacagcca taatgctctc ctgataatgt taaacttttt  120
tagtaaatca tctgctcgaa tacgagagta tagtcagtgc ggtgatgatt tgcttaacct  180
atgaaaatca aaagcttact cgcgctcaca ctcactgtga tttactaaaa gagtttaaac  240
attagagtta ttatctctaa tgcgtcactt ccaggtggcg taagcaagat tactcacttc  300
tgggtactga ttacgtgatc caaatcaaat ttttgcaaag ctgacacctt tcagcatcgc  360
ttttcgccat tatagctaac agttaataaa ttgtagtatg atttggtggc tacattagca  420
tgttttgcac aactagataa caataacgaa tgatagcaat tttaagtagt taggaggtga  480
aaaatgctgt caaaaggcgt attgtcagcg cgtcttttca accttattta tggctaacat  540
tatccggctt ttgcttcgga gctaaccgtg attcagacct tttttgattt tcccgtttac  600
ttcaaatttt tcatcgggtt atttgcgctg gtcaacccgg tagggattat tcccgtcttt  660
atcagcatga ccagttatca gacagcggca gcgcgaaaca aaactaacct tacagccaac  720
ctgtctgtgg ccattatctt gtggatctcg ctttttctcg gcgacacgat tctacaactt  780
tttggtatat caattgattc gttccgtatc gccgggggta tcctggtggt gacaatagcg  840
atgtcgatga tcagcggcaa gcttggcgag gataaacaga acaagcaaga aaaatcagaa  900
accgcggtac gtgaaagcat tggtgtggtg ccactggcgt tgccgttgat ggcggggcca  960
ggggcgatca gttctaccat cgtctggggt acgcgtta                          998

SEQ ID NO: 109          moltype = DNA  length = 999
FEATURE                 Location/Qualifiers
misc_feature            1..999
                        note = pflB_upstream
source                  1..999
                        mol_type = other DNA
                        organism = synthetic construct
SEQUENCE: 109
cagtgatgta ctgtttagcc agccagtcca tgaagtgatc catgcgctcc atcacttcat  60
catagttcag gacatcgcct ttgatcggtt cagacttcgg accaacctgc attttcagtt  120
tttcgtcaac gccgccgttg attgcgtaca gcatggtttt cgccaggttt gcacgcgcac  180
cgaagaactg catttgttta ccaacgatca tcgggcttac gcagcaagca atagcgtagt  240
catcgttgtt gaagtccgga cgcatcaggt catcgttctc atactgcaga gaagaggtgt  300
cgatggacac tttagcggcg aatttcttga agttcagcgg cagtttttca gaccacagaa  360
tggtcatgtt cggttccgga gacggaccca tggtgtacag ggtgttcagg aaacggaagc  420
tgtttttggt aaccagggta cgaccgtcga ggcccatacc accgatagat tcggttgccc  480
agatcgggtc gccagagaac agttcatcgt attccggagt acgcaggaag cgaaccatac  540
gcagtttcat gaccaggtgg tcaaccattt cctgcgcttc ttgttcggtg atcttgccag  600
ctttcaggtc acgttcgatg tacacatcca ggaaggtgga ggtacgaccg aaggacattg  660
cagcaccgtt ctgagactta acagcagcca ggtagccgaa gtaagtccac tggatagctt  720
cctgagcgtt ggtagccgga ccagagatgt cgtagccgta tttcgcagcc atttctttca  780
tctgacccag agcgcggtgc tgttcagcga tttcttcgcg cagacggata gtctgttcca  840
ggtttacgcc gttttccaga tcagcctgca gagaagtgaa ctgtgccagt ttgtctttca  900
tcaggtagtc gataccgtac agcgcaacgc gacggtagtc accgatgata cggccacggc  960
catatgcatc tggcagaccg gtcagaacac cagatttac                         999

SEQ ID NO: 110          moltype = DNA  length = 994
FEATURE                 Location/Qualifiers
misc_feature            1..994
                        note = pflB_downstream
source                  1..994
                        mol_type = other DNA
                        organism = synthetic construct
SEQUENCE: 110
gtaacaccta ccttcttaag tggatttttt atttactgcg tacttcgaca accattaatg  60
gtggtcgttt tcacgcaggt aaatgaccca gtatgtcaac ccaaccaaca aaccaccacc  120
gataatgttg ccgatcgtaa ccggaatcag gttatcagtg atgaaattca tcacggtcag  180
gtgagaaaaa ttttccggtg cagaaccgac tgcggtccaa aattccgggg atgcgaagtc  240
gcggattaca atacccatcg ggatcataaa catgtttgcg atactgtgct caaaaccgct  300
ggcaacaaac atcgcgaccg gcagcaccat aatgaacgct ttgtccatca ggctgcggcc  360
agaataactc atccatactg ccagacatac catcaggttt gccaggatac caagacagac  420
ggcctcaata aaagtatggt gcactttgtg gtcggcggtt tgtaggacgt ttagtcccca  480
ttgaccattt gcggtcatat actcgccgga aagccacatt aaaagtacaa acagcagtgc  540
gccgaccagg ttgccaaaat agacatttag ccagtttttc gccaactgac cccaggtgat  600
gcgcccactc gccttagcaa caacaatcaa cacggtggaa gtaaagagat cggctccgca  660
gacaacacaa agaatcagcc ccagagagaa gcaaatgccg ccaaccagtt ttgccatgcc  720
gaagggcatt gtgcctgtgc cagtggttgc tgtgatatag aagacgaatg cgattgagat  780
gaaaacaccg gcggtaatcg ccagatagaa agtcttaagc ggatgtttcg ttgctttata  840
gacacccgcc tcttcggcca ctttggccat tgcagcagga agtaaaagat caaaagggtt  900
gtcagctttc acactaactc tctctttatt aagtcggcga cgagatacta acaaagcatt  960
atagatgaga aattgatata gatcatatct cgcc                              994

SEQ ID NO: 111          moltype = DNA  length = 997
```

```
FEATURE               Location/Qualifiers
misc_feature          1..997
                      note = aldA_upstream
source                1..997
                      mol_type = other DNA
                      organism = synthetic construct
SEQUENCE: 111
atgcaccacg ctggttaagt tatcccggat tcgttcctca gttaggaaat aacgcagaca  60
gtgtaatctt tattaatcag ttacaaggat tatggccagt tgagcgttat ctctcactac  120
tcactggcga gctgccgcgt ttacgcgatg atagcgatgg ctacggtccc cgcgggcgag  180
attttatcgt tcacgttgat tttccggcag aagtcatcca tgcatggcaa acgctgaaac  240
atgatgcggt gctcatcgag gcgatggaaa gtcgctcgtt acgttaaaaa ttgcccgttt  300
gtgaaccact tgtttgcaaa cgggcatgac tcctgacttt tatttctgcc ttttattcct  360
tttacacttg tttttatgaa gcccttcaca gaattgtcct ttcacgattc cgtctctctg  420
atgattgatg ttaattaaca atgtattcac cgaaaacaaa catataaatc acaggagtcg  480
cccatgtcag tacccgttca acatcctatg tatatcgatg gacagtttgt tacctggcgt  540
ggagacgcat ggattgatgt ggtaaaccct gctacagagg ctgtcatttc ccgcataccc  600
gatggtcagg ccgaggatgc ccgtaaggca atcgatgcag cagaacgtgc acaaccagaa  660
tgggaagcgt tgcctgctat tgaacgcgcc agttggttgc gcaaaatctc cgccgggatc  720
cgcgaacgcg ccagtgaaat cagtgcgctg attgttgaag aagggggcaa gatccagcag  780
ctggctgaag tcgaagtggc ttttactgcc gactatatcg attacatggc ggagtgggca  840
cggcgttacg agggcgagat tattcaaagc gatcgtccag gagaaaatat tcttttgttt  900
aaacgtgcgc ttggtgtgac taccggcatt ctgccgtgga acttcccgtt cttcctcatt  960
gcccgcaaaa tggctcccgc tcttttgacc ggtaata                            997

SEQ ID NO: 112        moltype = DNA  length = 999
FEATURE               Location/Qualifiers
misc_feature          1..999
                      note = aldA_downstream
source                1..999
                      mol_type = other DNA
                      organism = synthetic construct
SEQUENCE: 112
aaacctttgg cccggtgctg ccagttgtcg catttgacac gctggaagat gctatctcaa  60
tggctaatga cagtgattac ggcctgacct catcaatcta tacccaaaat ctgaacgtcg  120
cgatgaaagc cattaaaggg ctgaagtttg gtgaaactta catcaaccgt gaaaacttcg  180
aagctatgca aggcttccac gccggatggc gtaaatccgg tattggcggc gcagatggta  240
aacatggctt gcatgaatat ctgcagaccc aggtggttta tttacagtct taatgagtga  300
aagaggcgga ggtttttttcc tccgcctgtg cgcgtcagag tttagcgaat ttttcgaggg  360
tgcgaataag ctgtgtgacg aagccatatt cgttatcgta ccaggcgacc gttttcacca  420
gttgtaaatc gcccacggcg gtaatttccg tttgcgtggc atcaaacacc gaaccgaaat  480
ggctgccaat gatatcggaa gagactattt cttcatcggt ataaccaaat gactcgttat  540
tggtggttgc ttgtttaagt gcgttattca cctcttcggc agtcactttt ttccgagaat  600
cgataccagt tcagtgaccg aacctgtttt caccggcacg cgttgcgcat gacctttcag  660
tttgccgctc agttccggga tcaccagacc aatggctttt gccgcccccg tagtgtgggg  720
aatgatattt tctgccgctg cgcgtgaagc acgtaaatct ttaccacgcg ggccatccac  780
cagtgactgg gtgccagtat aggcatgaat ggtcgtcatc gtgccgactt ctatcccgaa  840
actgtcatgc aaggctttgg ccatcggcgc aagacagtta gtggtgcatg acgccacgga  900
aacaatggtg tcgttgccat ccagagtgtc gtcattgacg ttataaacga tagttttcat  960
ttcaccggca ggggcggaaa tcaacacctt cttcgcacc                          999

SEQ ID NO: 113        moltype = DNA  length = 25
FEATURE               Location/Qualifiers
misc_feature          1..25
                      note = fhuA_For
source                1..25
                      mol_type = other DNA
                      organism = synthetic construct
SEQUENCE: 113
tggaccatgc agcaggtggt acaac                                        25

SEQ ID NO: 114        moltype = DNA  length = 21
FEATURE               Location/Qualifiers
misc_feature          1..21
                      note = fhuA_Rev
source                1..21
                      mol_type = other DNA
                      organism = synthetic construct
SEQUENCE: 114
gtttgccgtc cagttcgacg a                                            21

SEQ ID NO: 115        moltype = DNA  length = 25
FEATURE               Location/Qualifiers
misc_feature          1..25
                      note = fadL_For
source                1..25
                      mol_type = other DNA
                      organism = synthetic construct
```

```
SEQUENCE: 115
gtacgtaaac cgctaacaat ggcga                                          25

SEQ ID NO: 116         moltype = DNA  length = 21
FEATURE                Location/Qualifiers
misc_feature           1..21
                       note = fadL_Rev
source                 1..21
                       mol_type = other DNA
                       organism = synthetic construct
SEQUENCE: 116
gtttgccgtc cagttcgacg a                                              21

SEQ ID NO: 117         moltype = DNA  length = 25
FEATURE                Location/Qualifiers
misc_feature           1..25
                       note = adhE_For
source                 1..25
                       mol_type = other DNA
                       organism = synthetic construct
SEQUENCE: 117
ttcgggaact tgtagatacg tttac                                          25

SEQ ID NO: 118         moltype = DNA  length = 21
FEATURE                Location/Qualifiers
misc_feature           1..21
                       note = adhE_Rev
source                 1..21
                       mol_type = other DNA
                       organism = synthetic construct
SEQUENCE: 118
gtttgccgtc cagttcgacg a                                              21

SEQ ID NO: 119         moltype = DNA  length = 23
FEATURE                Location/Qualifiers
misc_feature           1..23
                       note = pflB_For
source                 1..23
                       mol_type = other DNA
                       organism = synthetic construct
SEQUENCE: 119
gtacttgtcg tgcatgtagt gga                                            23

SEQ ID NO: 120         moltype = DNA  length = 21
FEATURE                Location/Qualifiers
misc_feature           1..21
                       note = pflB_Rev
source                 1..21
                       mol_type = other DNA
                       organism = synthetic construct
SEQUENCE: 120
gtttgccgtc cagttcgacg a                                              21

SEQ ID NO: 121         moltype = DNA  length = 18
FEATURE                Location/Qualifiers
misc_feature           1..18
                       note = aldA_For
source                 1..18
                       mol_type = other DNA
                       organism = synthetic construct
SEQUENCE: 121
gttccgccgt atgactgg                                                  18

SEQ ID NO: 122         moltype = DNA  length = 21
FEATURE                Location/Qualifiers
misc_feature           1..21
                       note = aldA_Rev
source                 1..21
                       mol_type = other DNA
                       organism = synthetic construct
SEQUENCE: 122
gtttgccgtc cagttcgacg a                                              21
```